(12) United States Patent
Carter et al.

(10) Patent No.: US 8,927,732 B2
(45) Date of Patent: Jan. 6, 2015

(54) BIOTIN STANNANE FOR HPLC-FREE RADIOIODINATION

(75) Inventors: Randall Lee Carter, Clifton Park, NY (US); Bruce Fletcher Johnson, Scotia, NY (US); Anup Sood, Clifton Park, NY (US); Michael James Rishel, Saratoga Springs, NY (US); John Fitzmaurice Valliant, Ancaster (CA); Karin Ann Stephenson, Burlington (CA); Tao Wu, Ancaster (CA); Yang Yang, Edmonton (CA)

(73) Assignee: General Electric Company, Niskayuna, NY (US)

( * ) Notice: Subject to any disclaimer, the term of this patent is extended or adjusted under 35 U.S.C. 154(b) by 253 days.

(21) Appl. No.: 13/435,142

(22) Filed: Mar. 30, 2012

(65) Prior Publication Data
US 2013/0261311 A1    Oct. 3, 2013

(51) Int. Cl.
*C07F 7/22*       (2006.01)
*C07B 59/00*      (2006.01)

(52) U.S. Cl.
USPC .......................................................... 548/103

(58) Field of Classification Search
CPC ...... C07F 7/2212; C07F 7/2296; C07B 59/00
USPC .......................................................... 548/103
See application file for complete search history.

(56) References Cited

U.S. PATENT DOCUMENTS

| 7,335,347 B2 | 2/2008 | Valliant et al. |
| 7,521,531 B2 | 4/2009 | Govindan |
| 2007/0148647 A1 | 6/2007 | Luthra et al. |
| 2008/0305042 A1 | 12/2008 | Gacek et al. |
| 2010/0105888 A1 | 4/2010 | Husbyn |
| 2011/0033379 A1 | 2/2011 | Frangioni et al. |
| 2011/0137063 A1 | 6/2011 | Srinivasan et al. |

FOREIGN PATENT DOCUMENTS

| EP | 2110367 A1 | 10/2009 |
| WO | 2004035744 A2 | 4/2004 |

OTHER PUBLICATIONS

Hunter et al., "Polymer-Supported Radiopharmaceuticals: [131I]MIBG and [123I]MIBG", Journal of Labelled Compounds and Radiopharmaceuticals, vol. 42, Issue 7, pp. 653-661, Jul. 1999.
Donovan et al., "A New Strategy for Preparing Molecular Imaging and Therapy Agents Using Fluorine-Rich (Fluorous) Soluble Supports", Journal of the American Chemical Society, vol. 128, Issue 11, pp. 3536-3537, Feb. 25, 2006.
Search Report and Written Opinion from corresponding PCT Application No. PCT/EP2013/056699 dated Jun. 14, 2013.
Kabalka et al., Journal of Labelled Compounds and Radiopharmaceuticals, vol. 44, No. 13, pp. 921-929, 2001.

*Primary Examiner* — Joseph Kosack
(74) *Attorney, Agent, or Firm* — Eileen B. Gallagher

(57) ABSTRACT

The present teachings provide methods that enable the preparation and purification of radioiodinated vectors without the need for HPLC purification, as well as novel precursors which include biotin-like substituents useful in such methods.

27 Claims, 5 Drawing Sheets

BIOTIN STANNANE FOR HPLC-FREE RADIOIODINATION

BACKGROUND

Radioiodinated vectors are valuable tools for therapeutic, medical diagnostic imaging and research. For example, $^{123}$I labeled vectors are used for SPECT imaging, $^{124}$I labeled vectors are used PET imaging, $^{125}$I labeled vectors are used for biological assays and therapy and $^{131}$I labeled vectors are used for therapy.

Radioiodination (see Scheme 1, below) can be achieved by treatment of a vinyl or aryl-tin precursor ("Prec") with a radioiosotope of iodide (e.g., an $^{123}$I$^-$ species) under oxidative conditions to yield the desired radioiodinated product ("I-Prod") and a tin cleavage product ("C"). Excess aryl-tin precursor is used to ensure fast and efficient utilization of the radioactive iodide.

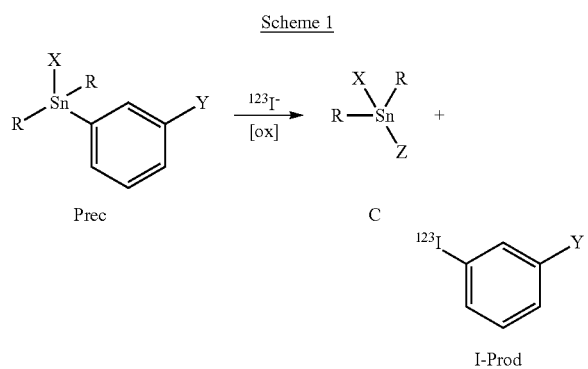

Scheme 1

Typically, HPLC is required to separate the desired radioiodinated product from the tin cleavage product and unreacted aryl-tin precursor. However, HPLC is time consuming, thus resulting in a loss of activity, and also generally requires significant investment, space and trained personnel.

SUMMARY OF THE INVENTION

The present teachings provide methods for the preparation and purification of radioiodinated vectors without the need for HPLC purification and novel precursors for use in such methods. Without wishing to be bound by any particular theory, it is believed that such methods would be advantageous, not only in saving time and cost, but also in maximizing the utilization of starting radioisotope and maintaining optimal radioactivity of the product.

In some embodiments, the present teachings provide a method of preparing a radioiodinated compound, the method comprising: contacting a biotin-containing tin precursor with a radioactive iodide and an oxidant to form a reaction mixture comprising a radioiodinated compound, unreacted precursor and reaction byproducts; and contacting the reaction mixture with avidin or streptavidin; thereby separating the radioiodinated compound from the precursor and the reaction byproducts.

In some embodiments, the present teachings provide a compound of formula (I):

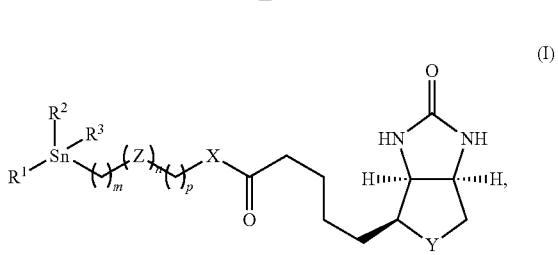

or a pharmaceutically acceptable salt thereof; wherein:
$R^1$ is an aromatic or vinyl group capable of being substituted at an aromatic or vinylic carbon with iodide;
$R^2$ and $R^3$ are each independently selected from $R^1$; alkyl or alkoxyalkyl, each substituted with 0-4 $R^5$ groups; or $R^2$ and $R^3$, along with the Sn atom to which they are attached, form a 3 to 8-membered ring that optionally includes one or more heteroatom selected from N, O, or S;
Z is selected from —(C$_1$-C$_4$)alkylene-, —(C$_1$-C$_4$)alkylene-O—, arylene, heteroarylene, cycloalkylene or heterocycloalkylene, provided that m is at least 1 when Z is arylene or heteroarylene;
X is selected from —O—, and —NR$^4$—;
$R^4$ is selected from H and alkyl, wherein the alkyl is substituted with 0-4 $R^6$ groups;
each $R^5$ is independently selected from —H, -halogen, —CN, —NO$_2$, —NR$^a$R$^b$, —OR$^c$, —S(O)$_i$R$^c$, —C(=O)R$^c$, —C(=O)OR$^c$ and —OC(=O)R$^c$;
$R^6$ is selected from —H, -halogen, —CN, —NO$_2$, —NR$^a$R$^b$, —OR$^c$, —S(O)$_i$R$^c$, —C(=O)R$^c$, —C(=O)OR$^c$ and —OC(=O)R$^c$;
$R^a$, $R^b$ and $R^c$ are each independently selected from —H and (C$_1$-C$_6$)alkyl;
Y is selected from S, SO, SO$_2$ and O;
i is 0, 1 or 2; and
m, n and p are each independently an integer from 0 to 10, wherein m+n+p≥1.

In a particular embodiment of Formula (I) or (A), m, n and p are each independently an integer from 0 to 10, wherein m+n+p≥2.

In a particular embodiment of Formula (I) or (A), $R^2$ and $R^3$ are both H.

In a particular embodiment of Formula (I) or (A), m, n and p are each independently an integer from 0 to 10, wherein m+n+p≥2 and $R^2$ and $R^3$ are both H.

In some embodiments, the present teachings provide a compound of formula (I):

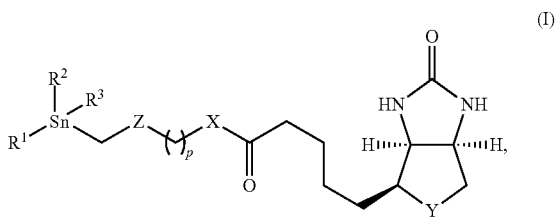

or a pharmaceutically acceptable salt thereof; wherein:
$R^1$ is an aromatic or vinyl group capable of being substituted at an aromatic or vinylic carbon with iodide;
$R^2$ and $R^3$ are each independently selected from (C$_1$-C$_6$) alkyl or alkoxyalkyl; or $R^2$ and $R^3$, along with the Sn atom to which they attach, form a 4, 5 or 6-membered ring that optionally includes one or more heteroatom selected from N, O, or S;

Z is —($C_1$-$C_4$)alkylene-O—;

X is selected from O and NH;

Y is selected from S or $SO_2$; and p is an integer from 2 to 4.

DETAILED DESCRIPTION OF THE INVENTION

Figure 1:
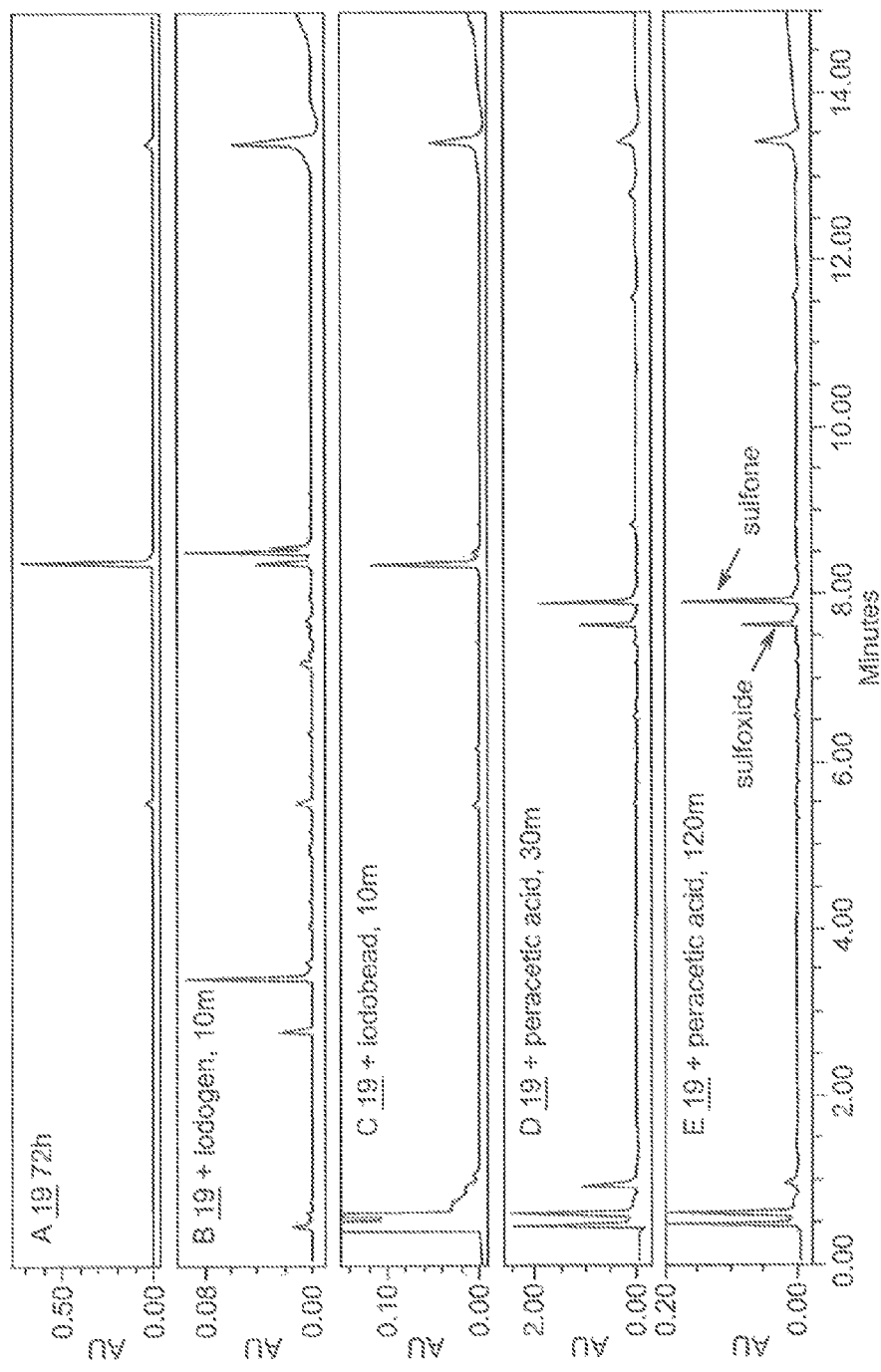
FIGS. 1A-1E are graphs demonstrating the stability of exemplary biotin precursors of the present teachings towards various oxidants used in radioiodination.

Sensitivity in PET and SPECT based medical imaging is dependent upon the amount of radioactivity localized at the site of interest and consequently upon the radioactivity per dose of agent or "specific activity" of the agent. It is important to maximize the chemical purity of a PET and SPECT imaging agents to ensure patient safety and to achieve high effective specific activity. Effective specific activity is defined as the moles of radiolabeled agent divided by the moles of all molecules with similar biological properties to the radiolabeled agent. Because an excess of Prec is used in radioiodinations, unreacted Prec is the primary source of low specific activity. For the imaging of low-abundance receptors, unreacted Prec can saturate the receptor and reduce binding of the radiolabeled product I-Prod which results in poor image quality.

It is also important to maximize the chemical purity of a PET and/or SPECT imaging agent to ensure patient safety. Current approaches to enhance the chemical purity of radioiodinated compounds rely on HPLC purification which is time-consuming thus leading to decay of radioactivity, limited by the ability to chromatographically separate the radioiodinated product from the precursor and expensive. The present teachings describe a method for the preparation and purification of radioiodinated vectors without the use of HPLC purification that achieve a high chemical purity of the radioiodinated vector.

An HPLC-free process that works on a broad range of compounds including biomolecules like peptides and antibodies would be advantageous. See, e.g., Eersels, J. L. H. et al., *Journal of Labelled Compounds and Radiopharmaceuticals*, 2005. 48(4): p. 241-257 and Coenen, H. H. et al., *Radioiodination Reactions for Pharmaceuticals* 2006: Springer. p. 101. The need for an HPLC-free process is recognized, however two reported solutions have significant drawbacks.

The first documented approach uses an insoluble resin or polymer as X (as depicted in Scheme 1). The precursor Prec consists of the vector attached to the resin via a tin linker. Upon oxidative radioiodination, the desired radioiodinated I-Prod is released during reaction and can be separated from Prec and C via filtrations. See, e.g., Culbert, P. A. et al., *Reactive Polymers*, 1993. 19(3): p. 247-253; Hunter, D. H. et al., *Journal of Labelled Compounds and Radiopharmaceuticals*, 1999. 42(7): p. 653-661 and Kabalka, G. W. et al., *Journal of Labelled Compounds and Radiopharmaceuticals*, 2001. 44(13): p. 921-929. However, this approach suffers from several drawbacks. For example, preparation, purification and characterization of the resin-bound precursor are difficult, particularly for a radiopharmaceutical where purity and sterility must be demonstrated to regulatory agencies in order to obtain approval. Additionally, chemistry on a resin is often not as facile as solution-phase chemistry and it is not clear that this approach would work for a sensitive large biomolecule, such as an antibody.

In a second approach, X (as depicted in Scheme 1) is a fluorous phase tail, such as $CF_3(CF_2)_5CH_2CH_2$—. After radioiodination, the desired I-Prod is isolated via elution through a fluorous-phase sep-pak on which Prec and C are retained because of the fluorous phase tail. See, e.g., Donovan, A. C. et al., *Nucl Med Biol*, 2008. 35(7): p. 741-6; Donovan, A. et al., *J Am Chem Soc*, 2006. 128(11): p. 3536-3537; and Valliant, J. F. et al., U.S. Pat. No. 7,335,347 B2, (2008). To maximize interaction with the fluorous phase the Sn bears 3 fluorous phase tails. However, this approach also suffers from several disadvantages. For example, if the vector is a large molecule, e.g., a peptide or antibody, it is unlikely that the precursor would be retained on the fluorous phase sep-pak because the chromatographic properties of the precursor would be dominated by the large vector, not the fluorous phase tails.

The present teachings relate to novel precursors for radioiodination and methods to prepare and purify radioiodinated vectors using these precursors, e.g., for the purpose of research, diagnostic imaging and therapy. Without wishing to be bound by any particular theory, it is believed that such methods and precursors have many advantages over the art, including but not limited to: elimination of the need for HPLC to purify the radioiodinated vector from the precursor and cleavage product; easy preparation, ability to characterize and purify the precursors, as they are single compounds; utility toward a broad range of radioiodinated vectors, including large molecules such as peptides or antibodies where chromatographic differentiation of the precursor and radioiodinated vector is minimal; and compatibility of precursors with an aqueous reaction mixture.

Methods of Preparation and Purification

In at least one embodiment, the present teachings provide methods for preparing or purifying a radioiodinated compound. Such methods generally include contacting a biotin-containing tin precursor with a radioactive iodide and an oxidant to form a reaction mixture comprising a radioiodinated compound, unreacted precursor and reaction byproducts; and contacting the reaction mixture with avidin or streptavidin to separate the radioiodinated compound from the precursor and the reaction byproducts. In at least one embodiment, the method further comprises contacting the reaction mixture with a solubility enhancing agent.

In at least one embodiment, the present teachings provide methods for preparing or purifying a radioiodinated compound. Such methods generally include contacting a biotin-containing tin precursor with a radioactive iodide, an oxidant and a solubility enhancing agent to form a reaction mixture comprising a radioiodinated compound, solubility enhancing agent, unreacted precursor and reaction byproducts; and contacting the reaction mixture with avidin or streptavidin to separate the radioiodinated compound from the precursor and the reaction byproducts.

In at least one embodiment, the present teachings provide methods for preparing or purifying a radioiodinated compound. Such methods generally include contacting a biotin-containing tin precursor with a radioactive iodide, and an oxidant to form a reaction mixture comprising a radioiodinated compound, unreacted precursor and reaction byproducts; and contacting the reaction mixture with a solubility enhancing agent and avidin or streptavidin to separate the radioiodinated compound from the precursor and the reaction byproducts.

In at least one embodiment, the present teachings provide methods for preparing or purifying a radioiodinated compound. Such methods generally include contacting a biotin-containing tin precursor with a radioactive iodide and an oxidant to form a reaction mixture comprising a radioiodinated compound, unreacted precursor and reaction byproducts; contacting the reaction mixture with a reductant to form a reduced reaction mixture; contacting the reduced reaction mixture with avidin or streptavidin to separate the radioiodinated compound from the precursor and the reaction byproducts. In at least one embodiment, the method further comprises the step of contacting the reaction mixture or the reduced reaction mixture with a solubility enhancing agent.

In at least one embodiment, the present teachings provide methods for preparing or purifying a radioiodinated compound. Such methods generally include contacting a biotin-containing tin precursor with a radioactive iodide, an oxidant and a solubility enhancing agent to form a reaction mixture comprising a radioiodinated compound, solubility enhancing agent, unreacted precursor and reaction byproducts; contacting the reaction mixture with a reductant to form a reduced reaction mixture; contacting the reduced reaction mixture with avidin or streptavidin to separate the radioiodinated compound from the precursor and the reaction byproducts.

In at least one embodiment, the present teachings provide methods for preparing or purifying a radioiodinated compound. Such methods generally contacting a biotin-containing tin precursor with a radioactive iodide and an oxidant to form a reaction mixture comprising a radioiodinated compound, unreacted precursor and reaction byproducts; contacting the reaction mixture with a reductant to form a reduced reaction mixture; contacting the reduced reaction mixture with a solubility enhancing agent and avidin or streptavidin to separate the radioiodinated compound from the precursor and the reaction byproducts.

Under typical reaction conditions the residual unbound radioiodine is minimal. In the event that radioiodine is not completely consumed by the reaction it is understood that pre or post purification of the residual unbound radioiodine with solid phase extraction techniques or others would be obvious to someone skilled in the art. This may include but are not limited to ionic exchange, silica gel, alumina, reverse-phase resins etc.

It is understood that contact with the solubility enhancing agent can be made at any time during the methods described herein. For example, the biotin-containing tin precursor can be contacted with a solubility enhancing agent during the formation of the reaction mixture, or alternatively, the reaction mixture may be formed as described above and after a period of time, the reaction mixture may be contacted with a solubility enhancing agent. Similarly, the biotin-containing tin precursor can be contacted with a solubility enhancing agent during the formation of the reaction mixture and prior to contact with the reductant, or alternatively, the reaction mixture may be formed as described above and after a period of time, the reaction mixture may be contacted with a solubility enhancing agent and then the reductant or with the solubility enhancing agent and the reductant contemporaneously. Similarly, when the reduced reaction mixture is contacted with a solubility enhancing agent, the contact may occur before, contemporaneously, or after contact with avidin or streptavidin. One of skill in the art is able to determine the appropriate timing of the above.

As used herein the term "radioiodinated compound" or "isolated radioiodinated compound" refers to aromatic or vinylic compounds, which include a radioactive iodine substituent on an aromatic or vinylic portion of the compound. Examples of radioactive iodine substituents include $^{123}$I, $^{124}$I, $^{125}$I and $^{131}$I. Accordingly, in some embodiments, the radioiodinated compound comprises an aryl moiety, such as an aryl acid. Exemplary radioiodinated compounds include, but are not limited to a radioiodinated benzoic acid, a radioiodinated benzamide, a radioiodinated benzylamine, and a radioiodinated benzylguanidine.

As used herein, "biotin" includes biotin, oxidation products of biotin, and biotin-like substituents, including, for example, biotin, oxybiotin, biotin sulfone and biotin sulfoxides, as well as stereoisomers thereof that bind to avidin or streptavidin. As used herein, the term "biotin-containing tin precursor" refers to a tin complex which includes a biotin, oxidation products of biotin, or a biotin-like substituent, as well as an aromatic or vinylic group capable of being labeled with iodide at an aromatic or vinylic carbon and bind to avidin or streptavidin. The tin molecule is attached by direct bond to a carbon atom of at least one aromatic or vinylic carbon. The tin molecule is also attached, via direct bond or via a linker, to a biotin, an oxidation product of biotin, or biotin-like substituent.

As used herein, the term "biotin-containing byproducts" or "reaction byproducts" refers to products of the reaction of an iodide and a biotin-containing precursor as defined herein. This reaction generally causes cleavage of the tin moiety from the aromatic vector capable of being labeled with iodide. Such by-products typically include a tin moiety attached, either directly or via a linker, to a biotin or biotin-like substituent.

In some embodiments, the oxidant is selected from iodogen and peracetic acid. For example, the oxidant can be a solid or in solution or suspension, or the oxidant can be pre-coated onto a tube or bead. In some embodiments, the radioactive iodide is selected from $^{123}$I, $^{124}$I, $^{125}$I, and $^{131}$I.

As used herein, the term "solubility enhancing agents" refers to molecules which enhance the solubility of organic molecules in water or mixtures of water and organic cosolvents. These typically are amphiphilic, containing a hydrophobic region and hydrophilic regions. Exemplary solubility enhancing agents include but are certainly not limited to: polysorbate 80 (Tween 80), cyclodextrins (for example α, β, γ cyclodextrins), analogs of cyclodextrin such as hydroxypropyl-β-cyclodextrin, and sodium lauryl sulfates.

As used herein, the term "reductant" refers to an agent which reduces the added oxidant and any remaining unreacted electrophilic radioiodine species. Exemplary reductants include but are not limited to sodium bisulfite, sodium thiosulfite or sodium metabisulfite.

In some embodiments, the biotin-containing tin precursor is compound represented by formula (A):

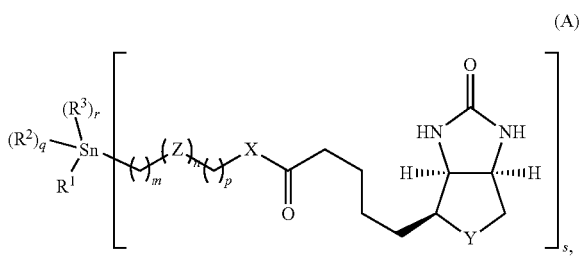

(A)

or a pharmaceutically acceptable salt thereof; wherein:

$R^1$ is an aromatic or vinyl group capable of being substituted at an aromatic or vinylic carbon with iodide;

$R^2$ and $R^3$ are each independently selected from $R^1$; alkyl or alkoxyalkyl, each substituted with 0-4 $R^5$ groups; or $R^2$ and $R^3$, along with the Sn atom to which they are attached, form a 3 to 8-membered ring that optionally includes one or more heteroatom selected from N, O, or S;

Z is selected from —($C_1$-$C_4$)alkylene-, —($C_1$-$C_4$)alkylene-O—, arylene, heteroarylene, cycloalkylene or heterocycloalkylene, provided that m is at least 1 when Z is arylene or heteroarylene and n=1 to 9, and provided that p=2-10 when Z is —($C_1$-$C_4$)alkylene-O—;

X is selected from —O—, and —$NR^4$—;

$R^4$ is selected from H and alkyl, wherein the alkyl is substituted with 0-4 $R^6$ groups;

each $R^5$ is independently selected from —H, -halogen, —CN, —$NO_2$, —$NR^aR^b$, —$OR^c$, —$S(O)_iR^c$, —$C(=O)R^c$, —$C(=O)OR^c$ and —$OC(=O)R^c$;

$R^6$ is selected from —H, -halogen, —CN, —$NO_2$, —$NR^aR^b$, —$OR^c$, —$S(O)_iR^c$, —$C(=O)R^c$, —$C(=O)OR^c$ and —$OC(=O)R^c$;

$R^a$, $R^b$ and $R^c$ are each independently selected from —H and ($C_1$-$C_6$)alkyl;

i is 0, 1, or 2;

Y is selected from S, SO, $SO_2$ and O;

m, n and p are each independently an integer from 0 to 10, wherein m+n+p≥1; and q and r are each individually an integer of 0 or 1; and s is an integer from 1 to 3, provided that q+r+s=3.

In other embodiments, the biotin-containing tin precursor is a compound represented by formula (I):

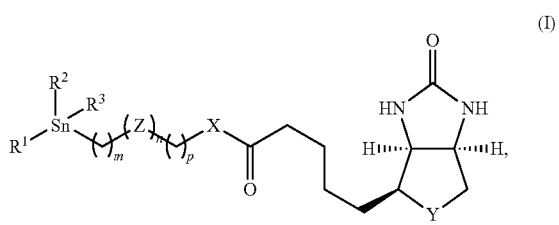

(I)

or a pharmaceutically acceptable salt thereof; wherein:

$R^1$ is an aromatic or vinyl group capable of being substituted at an aromatic or vinylic carbon with iodide;

$R^2$ and $R^3$ are each independently selected from $R^1$; alkyl or alkoxyalkyl, each substituted with 0-4 $R^5$ groups; or $R^2$ and $R^3$, along with the Sn atom to which they are attached, form a 3 to 8-membered ring that optionally includes one or more heteroatom selected from N, O, or S;

Z is selected from —($C_1$-$C_4$)alkylene-, —($C_1$-$C_4$)alkylene-O—, arylene, heteroarylene, cycloalkylene or heterocycloalkylene, provided that m is at least 1 when Z is arylene or heteroarylene, and n=1 to 9, and provided that p=2-10 when Z is —($C_1$-$C_4$)alkylene-O—;

X is selected from —O—, and —$NR^4$—;

$R^4$ is selected from H and alkyl, wherein the alkyl is substituted, with 0-4 $R^6$ groups;

each $R^5$ is independently selected from —H, -halogen, —CN, —$NO_2$, —$NR^aR^b$, —$OR^c$, —$S(O)_iR^c$, —$C(=O)R^c$, —$C(=O)OR^c$ and —$OC(=O)R^c$;

$R^6$ is selected from —H, -halogen, —CN, —$NO_2$, —$NR^aR^b$, —$OR^c$, —$S(O)_iR^c$, —$C(=O)R^c$, —$C(=O)OR^c$ and —$OC(=O)R^c$;

$R^a$, $R^b$ and $R^c$ are each independently selected from —H and ($C_1$-$C_6$)alkyl;

Y is selected from S, SO, $SO_2$ and O;

i is 0, 1, or 2; and m, n and p are each independently an integer from 0 to 10, wherein m+n+p≥1.

As used herein, an aromatic or vinyl group capable of being labeled with iodide means that the iodine moiety is attached to the aromatic (e.g. an aryl iodide) or vinylic group (e.g. vinyl iodide) to yield a therapeutic agent, a diagnostic agent or both. The term "aryl iodide" refers to an aromatic group directly bearing an iodide. The term "vinyl iodide" refers to a vinylic group directly bearing an iodide. In one embodiment, the aromatic vector capable of being labeled with iodide comprises a five- to fourteen-membered aryl moiety or a five- to fourteen-membered heteroaryl moiety.

As used herein, the term "vector" refers to an aromatic or vinyl group, wherein one of the aromatic or vinylic carbons atoms is substituted with iodide. As used herein, the phrase "aromatic vector" refers to a substance, e.g., a small molecule organic compound or a macromolecule, which includes at least one aromatic moiety. Thus, an "aromatic vector capable of being labeled with iodide" refers to an aromatic vector that is capable of exchanging at least one ring substituent with an iodide substituent.

As used herein, the phrase "vinylic vector" refers to a substance, e.g., a small molecule organic compound or a macromolecule, which includes at least one vinylic moiety. Thus, a "vinylic vector capable of being labeled with iodide" refers to a vinylic vector that is capable of exchanging at least one vinylic carbon substituent with an iodide substituent. In some embodiments, the aromatic or vinylic vector capable of being labeled with iodide yields (i.e., upon labeling with iodide) a therapeutic agent, a diagnostic agent or both.

As used herein, the term "therapeutic agent" refers to a drug, medicament, or other substance capable of producing an effect on a body; for example, an agent that can be used to prevent cure, alleviate the onset and/or progression of a condition, pathological disorder or disease. Therapeutic agents include low molecular weight drugs, proteins, peptides, oligonucleotides, nucleic acids, polysaccharides and other macromolecules, each of which can be synthetic or naturally produced. The term "drugs" includes small molecules, such as organic compounds, with a molecular weight of between about 50 and about 1000 daltons.

As used herein, the term "diagnostic agent" refers to a substance which permits the detection or monitoring of a physiological condition or function; for example, an agent that can be used to detect, image and/or monitor the presence and/or progression of a condition, pathological disorder or disease.

In some embodiments, $R^2$ and $R^3$ in Formulas A, I and/or II are each independently selected from ($C_1$-$C_6$)alkyl, e.g., methyl, ethyl, propyl, butyl, pentyl or hexyl or alkoxyalkyl, e.g. methoxymethyl, ethyoxyethyl, methoxymethoxymethyl, —CH$_2$CH$_2$CH$_2$OCH$_2$CH$_2$OCH$_3$. In some embodiments, R$^2$ and R$^3$ in Formulas A, I and/or II are each independently selected from methyl, ethyl, n-propyl or n-butyl.

In some embodiment, R$^2$ and R$^3$ in Formulas A, I and/or II, together with the Sn atom to which they are attached, form a 3 to 8 membered ring that optionally includes one or more heteroatom selected from N, O, or S. For example, the ring formed may be one of the following:

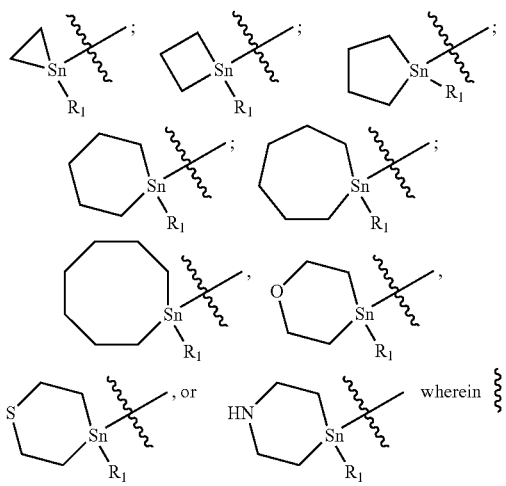

designates the attachment of the Sn atom to the remainder of the molecule; and wherein any one or more of the hydrogen atoms in the ring formed may be replaced with halogen, alkyl, —CN, —NO$_2$, —NR$^a$R$^b$, —OR$^c$, —S(O)$_i$R$^c$, —C(=O)R$^c$, —C(=O)OR$^c$ or —OC(=O)R$^c$.

In some embodiments of Formulas A, I and/or II, X is selected from O and NR$^4$; and R$^4$ is selected from H and (C$_1$-C$_6$)alkyl. For example, in some embodiments of Formulas A, I and/or II, X is selected from O and NH. In some embodiments, Y is selected from O, S, SO, and SO$_2$. For example, in some embodiments of Formulas A, I and/or II, Y is S. In other embodiments of Formulas A, I and/or II, Y is SO$_2$. In some embodiments of Formulas A, I and/or II, Z is selected from —(C$_1$-C$_4$)alkylene-, —(C$_1$-C$_4$)alkylene-O—. For example, in some embodiments of Formulas A, I and/or II, Z is —(C$_1$-C$_4$)alkylene-O—.

In some embodiments of Formulas A, I and/or II, m, n and p are each independently an integer from 0 to 5. For example, in some embodiments of Formulas A, I and/or II, m and n are both 0 and p is an integer from 2 to 4.

In some embodiments, R$^2$ and R$^3$ are each independently selected from (C$_1$-C$_6$)alkyl; X is selected from O and NR$^4$; Y is selected from S, SO, and SO$_2$; Z is selected from —(C$_1$-C$_4$)alkylene-, and —(C$_1$-C$_4$)alkylene-O—; R$^4$ is selected from H and (C$_1$-C$_6$)alkyl; and m, n and p are each independently an integer from 0 to 5.

In some embodiments of Formulas A, I and/or I$^1$, R$^2$ and R$^3$ are each independently selected from methyl, ethyl, n-propyl or n-butyl; X is selected from O and NH; Y is SO$_2$; Z is —(C$_1$-C$_4$)alkylene-O—; m and n are both 0 and p is an integer from 2 to 4.

In some embodiments, R$^2$ and R$^3$, together with the Sn atom form a 3, 4, 5, 6, 7, or 8 membered ring that optionally includes one or more heteroatom selected from N, O, or S; X is selected from O and NR$^4$; Y is selected from S, SO, and SO$_2$; Z is selected from —(C$_1$-C$_4$)alkylene-, and —(C$_1$-C$_4$) alkylene-O—; R$^4$ is selected from H and (C$_1$-C$_6$)alkyl; and m, n and p are each independently an integer from 0 to 5.

In some embodiments of Formulas A, I and/or II, R$^2$ and R$^3$, together with the Sn atom form a 5 or 6 membered ring that optionally includes one or more heteroatom selected from N, O, or S; X is selected from O and NH; Y is SO$_2$; Z is —(C$_1$-C$_4$)alkylene-O—; m and n are both 0 and p is an integer from 2 to 4.

For example, in some embodiments, the biotin-containing byproducts comprise at least one compound of formula (II):

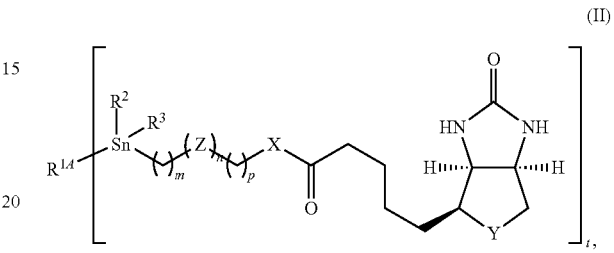

or a pharmaceutically acceptable salt thereof; wherein R$^2$-R$^6$, Z, X, Y, R$^a$, R$^b$, R$^c$, m, n and p are as defined above for formula (I) and various embodiments thereof; and wherein R$^{1A}$ is —OH and t is 1 or wherein R$^{1A}$ is —O— and t is 2.

In some embodiments, contacting the reaction mixture or the reduced reaction mixture with avidin or streptavidin comprises at least one of the following:

- passage of the reaction mixture or the reduced reaction mixture down a column of avidin or streptavidin solid support;
- mixing an avidin or streptavidin solid support with the reaction mixture or the reduced reaction mixture followed by filtering;
- depositing the biotin-containing precursor on an avidin or streptavidin solid support, followed by contacting the biotin-containing precursor with the radioactive iodide and the oxidant, followed by eluting the radioiodinated compound;
- treating the reaction mixture or the reduced reaction mixture with soluble avidin or streptavidin followed by size separation of avidin- or streptavidin-bound complexes from the radioiodinated compound; or
- passing the reaction mixture or the reduced reaction mixture over a streptavidin or avidin-coated surface.

The present invention provides a radioiodinated compound in a level of purity comparable to that achieved by conventional HPLC methods. The high level of purity permits the use of the radioiodiated compounds prepared by the methods disclosed herein to be used as a diagnostic or therapeutic agent. In some embodiments, such methods allow for the production of radioiodianated compounds having minimal impurities. For example, in some embodiments, the radioiodinated compound is in a composition comprising less than about 10%, less than about 5%, or less then about 1% biotin-containing precursors or biotin-containing byproducts. In some embodiments, the radioiodinated compound is in a composition comprising less than about 0.9%, less than about 0.8%, less than about 0.7%, less than about 0.6%, less than about 0.5%, less than about 0.4%, less than about 0.3%, less than about 0.2%, less than about 0.1%, or even less than about 0.05% biotin-containing precursors or biotin-containing byproducts. Generally, the major contaminant resulting in the preparation of the radioiodinated compound is the unreacted biotin-containing precursor and/or the biotin-containing byproducts. As such, because the methods disclosed herein are effective in separating the desired radioiodinated compound from the unreacted biotin-containing precursor and/or the biotin-containing byproducts, the resulting radioiodinated compound is at least 90%, at least 95%, at least 99%, at least 99.1%, at least 99.2%, at least 99.3%, at least 99.4%, at least 99.5%, at least 99.6%, at least 99.7%, at least 99.8%, at least 99.9% or at least 99.95% pure.

As used herein, the term "alkyl" refers to a saturated aliphatic straight-chain or branched monovalent hydrocarbon radical. Unless otherwise specified, an alkyl group typically has 1-6 carbon atoms, i.e. ($C_1$-$C_6$)alkyl. As used herein, a "($C_1$-$C_6$)alkyl" group is means a radical having from 1 to 6 carbon atoms in a linear or branched arrangement. An "alkylene group" is a saturated aliphatic branched or straight-chain divalent hydrocarbon radical. Unless otherwise specified, an alkylene group typically has 1-6 carbon atoms, i.e., ($C_1$-$C_6$) alkylene.

As used herein, the term "alkoxyalkyl" refers to an alkyl, wherein non-adjacent carbon atoms are replaced with oxygen. Examples of alkoxyalkyl include, for example, methoxymethyl, ethyoxyethyl, propoxymethyl, or —$CH_2CH_2CH_2OCH_2CH_2OCH_3$.

The term "aryl" refers to an aromatic hydrocarbon ring system. The term "aryl" may be used interchangeably with the terms "aryl moiety," "aryl ring" and "aryl group." An aryl group typically has six to fourteen ring atoms. "Aryl" includes monocyclic rings and polycyclic rings, in which a monocyclic aryl ring is fused to one or more other aryl rings. Examples of aryl groups include, but are not limited to, phenyl, naphthyl, anthracenyl, 1,2-dihydronaphthyl, 1,2,3,4-tetrahydronaphthyl, fluorenyl, indanyl, indenyl and the like. A "substituted aryl group" is substituted at any one or more substitutable ring atom. Arylene refers to a bivalent aryl radical.

The terms "heteroaryl," "heteroaryl ring," "heteroaryl group" and "heteroaryl moiety" are used interchangeably herein to refer to aromatic ring groups having typically five to fourteen ring atoms selected from carbon and at least one (typically 1 to 4, more typically 1 or 2) heteroatoms (e.g., oxygen, nitrogen or sulfur). "Heteroaryl" includes monocyclic rings and polycyclic rings in which a monocyclic heteroaromatic ring is fused to one or more other aryl or heteroaryl rings. Examples of monocyclic heteroaryl groups include, but are not limited to, furanyl (e.g., 2-furanyl, 3-furanyl), imidazolyl (e.g., N-imidazolyl, 2-imidazolyl, 4-imidazolyl, 5-imidazolyl), isoxazolyl (e.g., 3-isoxazolyl, 4-isoxazolyl, 5-isoxazolyl), oxadiazolyl (e.g., 2-oxadiazolyl, 5-oxadiazolyl), oxazolyl (e.g., 2-oxazolyl, 4-oxazolyl, 5-oxazolyl), pyrazolyl (e.g., 3-pyrazolyl, 4-pyrazolyl), pyrrolyl (e.g., 1-pyrrolyl, 2-pyrrolyl, 3-pyrrolyl), pyridyl (e.g., 2-pyridyl, 3-pyridyl, 4-pyridyl), pyrimidinyl (e.g., 2-pyrimidinyl, 4-pyrimidinyl, 5-pyrimidinyl), pyridazinyl (e.g., 3-pyridazinyl), thiazolyl (e.g., 2-thiazolyl, 4-thiazolyl, 5-thiazolyl), isothiazolyl, triazolyl (e.g., 2-triazolyl, 5-triazolyl), tetrazolyl (e.g., tetrazolyl), and thienyl (e.g., 2-thienyl, 3-thienyl). Examples of polycyclic aromatic heteroaryl groups include carbazolyl, benzimidazolyl, benzothienyl, benzofuranyl, isobenzofuranyl, indolyl, benzotriazolyl, benzothiazolyl, benzoxazolyl, quinolinyl, isoquinolinyl, indazolyl, isoindolyl, acridinyl, or benzisoxazolyl. A "substituted heteroaryl group" is substituted at any one or more substitutable ring atom, which is a ring carbon or ring nitrogen atom bonded to a hydrogen. Heteroarylene refers to a bivalent heteroaryl radical.

The term "cycloalkyl" refers to a monocyclic or polycyclic saturated hydrocarbon ring system. For example, a $C_5$-$C_7$ cycloalkyl includes, but is not limited to cyclopentyl, cyclohexyl or cycloheptyl, each of which is optionally substituted. Cycloalkylene refers to a bivalent cycloalkyl radical The term "heterocycloalkyl" refers to non-aromatic rings, generally with 3 to 10-members containing from 1-4 ring heteroatoms. Each heteroatom is independently selected from nitrogen, quaternary nitrogen, oxidized nitrogen (e.g., NO); oxygen; and sulfur, including sulfoxide and sulfone. Representative monocyclic heterocycloalkyl groups include morpholinyl, thiomorpholinyl, pyrrolidinonyl, pyrrolidinyl, piperidinyl, piperazinyl, hydantoinyl, valerolactamyl, oxiranyl, oxetanyl, tetrahydrofuranyl, tetrahydropyranyl, tetrahydropyrindinyl, tetrahydropyrimidinyl, tetrahydrothiophenyl, tetrahydrothiopyranyl, and the like. Heterocycloalkylene refers to a bivalent heterocycloalkyl radical.

EXEMPLIFICATION

Example 1

Synthesis of Precursors

Arylstannanes bearing biotin or biotin sulfone units were designed and prepared. Vinylic stannanes may be prepared by similar methods. 3-Stannyl benzoic acid/ester was selected as the model system since the corresponding radiolabeled product (3-iodobenzoic acid/ester) can be conjugated to other diagnostic and therapeutic vectors via simple chemical reactions. Though other linkages are possible an ester linkage between biotin and the arylstannane was chosen because esters are sufficiently stable under slightly acidic labeling conditions and because the precursor for the ester linkage (i.e., an alcohol) is readily accessible via established and generally high yielding reactions, e.g. hydroboration or ozonolysis.

Key intermediate 6 was prepared in high yield from commercially available $Bu_2SnCl_2$ (1) in good yield as shown in Scheme 2:

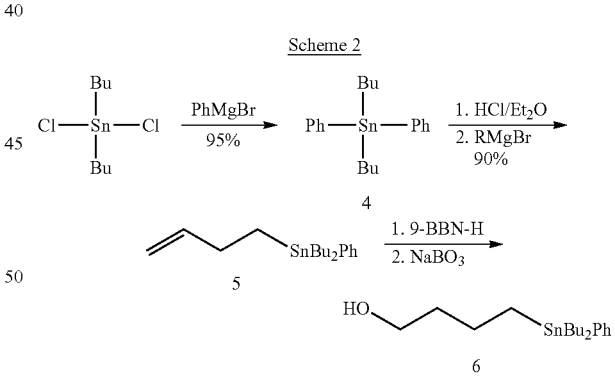

In brief, to a solution of dibutyltin dichloride (15.2 g, 50 mmol) in THF (50 mL) was added phenylmagnesium bromide (30 mL, 60 mmol, 2.0 M in THF) at 0° C. The resulting mixture was stirred at 0° C. for 1 h, then quenched with $NH_4Cl$ (50 mL, sat. aq.) and extracted with $Et_2O$ (100 mL×3). The combined organic extract was dried over $Na_2SO_4$ and concentrated. The oily residue was purified by flash column chromatography (silica gel, 100% hexanes) to afford compound 4 in 95% yield (18.4 g, 47.5 mmol).

Compound 4 (1.94 g, 5.0 mmol) was taken up in $Et_2O$ (5.0 mL) and cooled to 0° C. An anhydrous solution of HCl in $Et_2O$ (2.5 mL, 5.0 mmol, 2.0 M) was added dropwise. The resulting clear solution was allowed to warm to room temperature for 30 min. The Grignard reagent (15 mL, 7.5 mmol, 0.5 M in THF or Et$_2$O) was added at 0° C. and the resulting suspension stirred for another 1 h. After quenching with NH$_4$Cl (10 mL, sat. aq.) and extraction with Et$_2$O (10 mL×3), the combined organic extract was dried over Na$_2$SO$_4$ and concentrated. The oily residue was purified by flash column chromatography (silica gel, 100% hexanes) to afford compound 5 in 90% yield.

To a solution of compound 5 (1.46 g, 4.0 mmol) in THF (4.0 mL) was added 9-BBN-H (6.0 mL, 6.0 mmol, 1.0 M in THF) at 0° C. The reaction solution was allowed to warm to room temperature for 1 h. H$_2$O (10 mL) was added to the reaction mixture followed by NaBO$_3$ (1.63 g, 20 mmol). The resulting suspension was stirred vigorously at room temperature for 12 h before extraction with diethyl ether (20 mL×3). The combined organic extract was dried over Na$_2$SO$_4$ and concentrated. The oily residue was purified by flash column chromatography (silica gel, 1:1 hexanes/ethyl acetate) to afford compound 6 in 92% yield (1.41 g, 3.68 mmol).

As shown in Scheme 3, alcohol 6 was esterified with biotin or biotin sulfone to yield arylstannanes 7 and 8. The arylstannanes were treated with I$_2$ to produce Sn—I species, which were further reduced to the dimeric tin species 9 and 10 using a one-pot procedure.

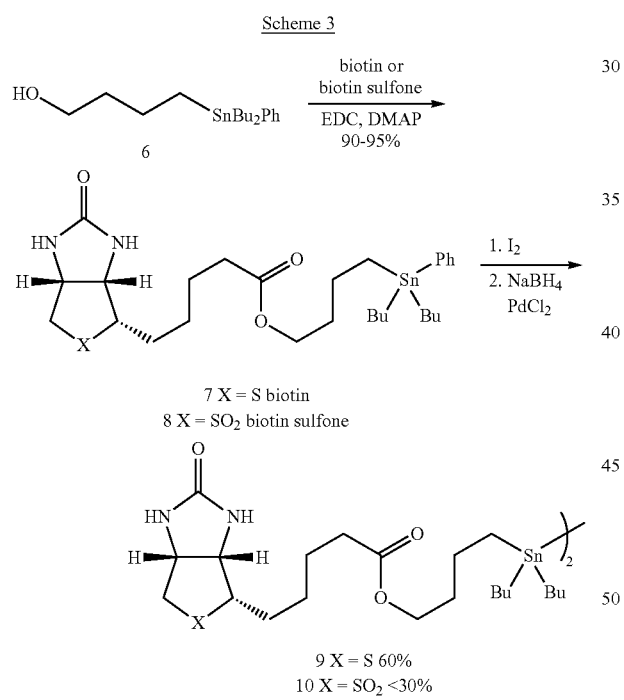

Scheme 3

Briefly, to a solution of compound 6 (383 mg, 1.0 mmol) in DMF (2.0 mL) were added biotin (366 mg, 1.5 mmol) or biotin sulfone (414 mg, 1.5 mmol), EDC.HCl (287 mg, 1.5 mmol), DMAP (cat.). The resulting solution (suspension for biotin sulfone) was stirred at room temperature for 12 h and volatiles were removed in vacuo. Purification was accomplished by flash column chromatography (silica gel, 10% MeOH/CH$_2$Cl$_2$) to afford the desired ester 7 or 8 in 90~95% yield.

To a solution of ester 7 (305 mg, 0.5 mmol) in CH$_2$Cl$_2$ (2.0 mL) was added I$_2$ (379 mg, 1.5 mmol) in portions at room temperature. The resulting brown solution was stirred at room temperature for another 30 min. NaBH$_4$ (113 mg, 3.0 mmol) was added followed by the dropwise addition of MeOH (1.0 mL). After bubbles faded away, PdCl$_2$ (0.9 mg, 0.005 mmol) was added to the colorless suspension. The resulting pale yellow suspension was stirred at room temperature for 1 h. Solvents were removed in vacuo and the residue was subjected to flash column chromatography (silica gel, 10% MeOH/CH$_2$Cl$_2$) to afford the desired ditin compound 9 (160 mg, 0.15 mmol, 60% yield) as a waxy solid. Compound 10 was synthesized in a similar manner, albeit in lower yield (<30%).

Alternatively, dimeric tin compounds 9 and 10 have also been prepared via esterification of 11 with biotin or biotin sulfone as shown in Scheme 4:

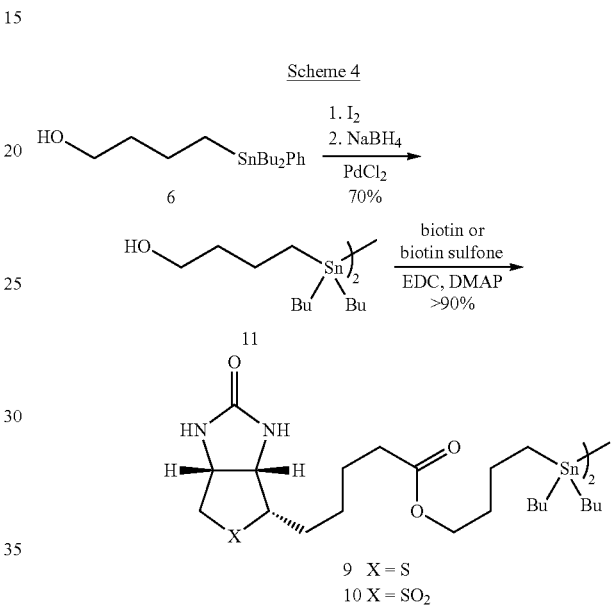

Scheme 4

Specifically, the ditin compound II was prepared using the procedure for the synthesis of compound 9. Esterification was done as for compound 7 to produce ditin 9 and 10 in >90% yield.

With species 9 and 10 in hand, Stille coupling conditions were explored using 12 and aryl iodide 13 as model compounds, as shown in Scheme 5. Excellent yields of model stannane 14 were observed with Pd(PPh$_3$)$_2$Cl$_2$/KOAc/NMP.

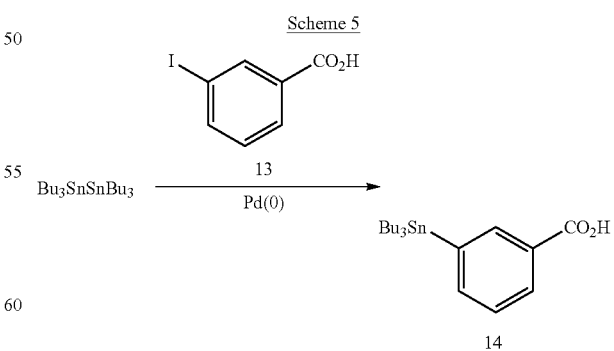

Scheme 5

Catalyst conditions:
Pd(Ph$_3$)$_4$, THF or DMF, heat or MW, 0%
Pd(OAc)$_2$, PA, THF, heat or MW 0%
Pd(PPh$_3$)$_2$Cl$_2$, KOAc, NMP, 91%

Specifically, to a degassed solution of 3-iodobenzoic acid 13 (49 mg, 0.2 mmol) in NMP (0.3 mL) were added KOAc (59 mg, 0.6 mmol) and Pd(PPh$_3$)$_2$Cl$_2$ (7 mg, 0.01 mmol). The resulting pale orange solution was stirred for 10 min followed by the addition of hexabutylditin 12 (290 mg, 0.5 mmol). After stirring at room temperature for 24 h, the dark red reaction mixture was diluted with diethyl ether (0.5 mL) and directly loaded on a silica gel column and flushed with 1:1 hexanes/ethyl acetate to afford the desired arylstannane 14 in 91% yield (75 mg, 0.182 mmol).

These same Stille coupling conditions were applied to biotin containing dimer 9 and biotin sulfone dimer 10 to yield the iodination precursors 15 and 2 in 60%-65% yield (purification was done by semi-prep HPLC), as shown in Scheme 6.

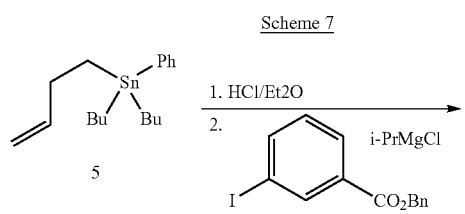

An alternative method of making aryl-tin bonds, involving nucleophilic addition of aryl Grignard reagents to tin-halogen species, was used to prepare benzyl protected tin-biotin 19 and tin-biotin sulfone 18 precursors, as shown in Scheme 7.

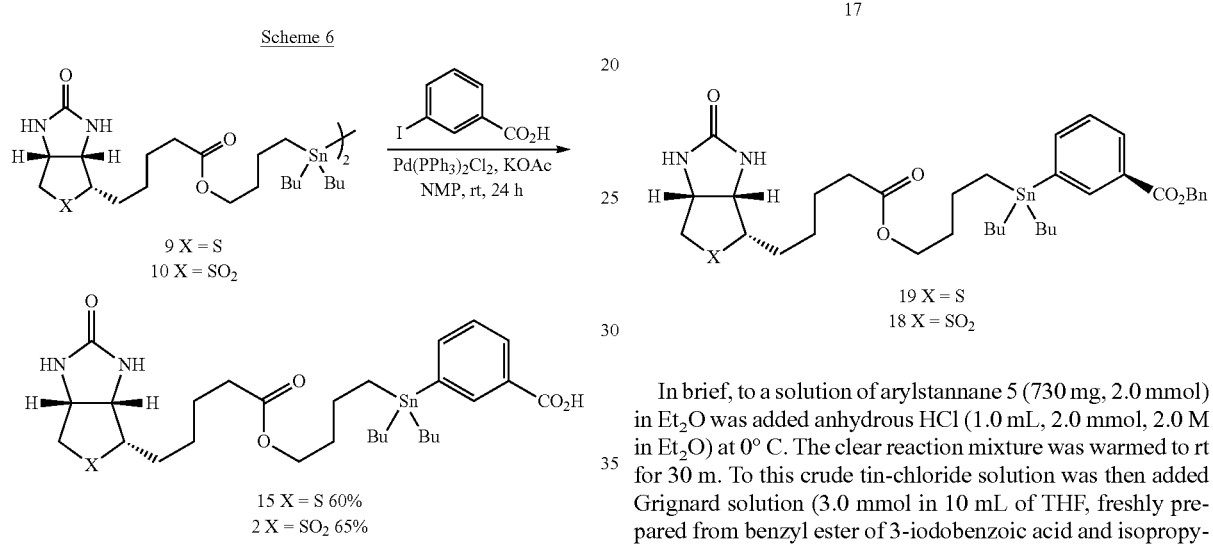

In brief, to a solution of arylstannane 5 (730 mg, 2.0 mmol) in Et$_2$O was added anhydrous HCl (1.0 mL, 2.0 mmol, 2.0 M in Et$_2$O) at 0° C. The clear reaction mixture was warmed to rt for 30 m. To this crude tin-chloride solution was then added Grignard solution (3.0 mmol in 10 mL of THF, freshly prepared from benzyl ester of 3-iodobenzoic acid and isopropylmagnesium chloride) at −20° C. The resulting gray suspension was allowed to warm to 0° C. for 2 h. NH$_4$Cl (10 mL, sat. aq.) was used to quench excess Grignard reagent and the reaction mixture was extracted with Et$_2$O (10 mL×3). The combined organic extract was dried over Na$_2$SO$_4$ and concentrated. Purification was accomplished by flash column chromatography (silica gel, 10% EtOAc/hexanes) to afford the desired arylstannane 16 in 75% yield (748 mg, 1.5 mmol).

Hydroboration of arylstannane 16 to yield alcohol 17 was done as for conversion of compound 5 to compound 6. Esterification of alcohol 17 was performed as for the syntheses of compounds 7 and 8 to produce compounds 19 (60%) and 18 (65%).

A PEG-chain modified precursor 22 was also prepared starting from Biotin-PEG-acid 21 and hydroxystannane 6 as shown in Scheme 8.

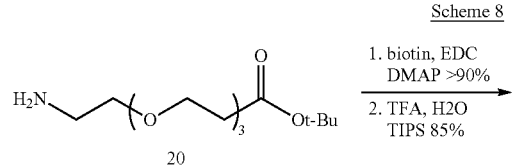

-continued

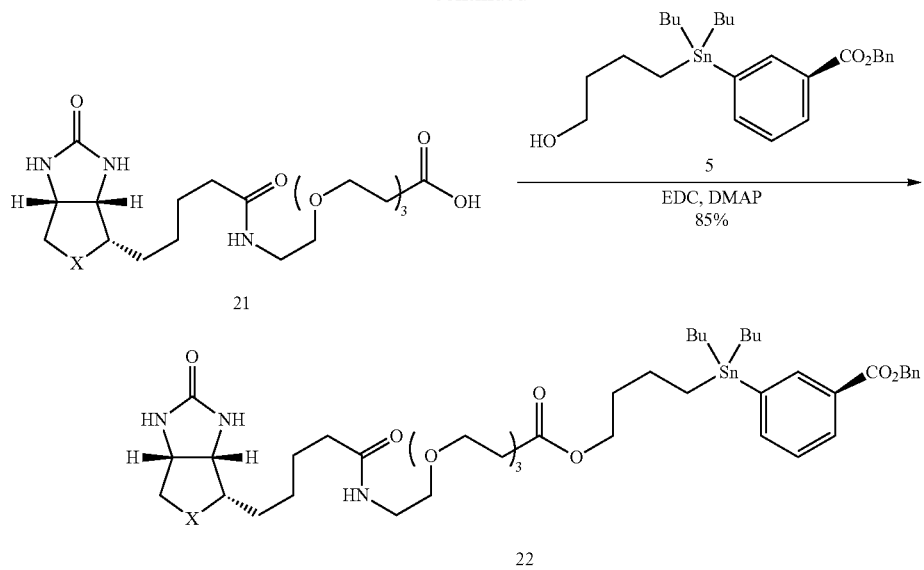

TABLE A

<sup></sup>¹H NMR data for compounds

| Compound | Chemical shifts | Solvent |
|---|---|---|
| 2 | 7.99 (1 H, s, $J_{Sn-C-C-H}$ = 40.0 Hz), 7.83 (1 H, d, J = 7.6, Hz), 7.54 (1 H, d, J = 7.1 Hz, $J_{Sn-C-C-H}$ = 37.6 Hz), 7.37 (1 H, dd, J = 7.6, 7.1 Hz, $J_{Sn-C-C-C-H}$ = 9.5 Hz), 6.77 (1 H, s, br), 6.61 (1 H, s, br), 4.44-4.35 (2 H, m), 4.00 (2 H, t, J = 6.0 Hz), 3.31 (1 H, dd, J = 14.1, 6.9 Hz), 3.15 (1 H, q, J = 6.9 Hz), 3.02 (1 H, d, J = 14.1 Hz), 2.25 (2 H, t, J = 7.5 Hz), 1.70-0.82 (30 H, m) | DMSO-$d_6$ |
| 5 | 7.47 (2 H, d, J = 7.3 Hz, $J_{Sn-C-C-H}$ = 38.4 Hz), 7.36-7.28 (3 H, m), 5.89 (1 H, ddt, J = 16.7, 10.1, 6.3 Hz), 5.01 (1 H, dd, J = 16.7, 1.1 Hz), 4.93 (1 H, dd, J = 10.1, 1.1 Hz), 2.32 (2 H, m), 1.63-0.84 (20 H, m). | CDCl$_3$ |
| 6 | 7.46 (2 H, d, J = 7.4 Hz, $J_{Sn-C-C-H}$ = 39.0 Hz), 7.35-7.27 (3 H, m), 3.64 (2 H, m), 1.70-0.85 (24 H, m) | CDCl$_3$ |
| 9 | 6.43 (2 H, s, br), 6.36 (2 H, s, br), 4.30 (2 H, dd, J = 7.5, 5.1 Hz, 1H), 4.12 (2 H, ddd, J = 7.5, 4.5, 1.8 Hz), 4.00 (4 H, t, J = 6.1 H), 3.08 (2 H, ddd, J = 8.6, 6.1, 4.5 Hz), 2.81 (2 H, dd, J = 12.4, 5.1 Hz), 2.58 (2 H, d, J = 12.4 Hz), 2.26 (4 H, t, J = 7.5 Hz), 1.64-0.84 (60 H, m) | DMSO-$d_6$ |
| 10 | 6.69 (2 H, s, br), 6.60 (2 H, s, br), 4.41 (2 H, dd, J = 10.2, 7.0 Hz), 4.41 (2 H, ddd, J = 10.2, 6.0, 1.8 Hz), 4.01 (4 H, t, J = 6.2 Hz), 3.30 (2 H, dd, J = 14.2, 7.0 Hz), 3.16 (2 H, q, J = 6.9 Hz), 3.02 (2 H, d, J = 14.2 Hz), 2.28 (4 H, t, J = 7.5 Hz), 1.72-0.82 (60 H, m) | DMSO-$d_6$ |
| 11 | 4.31 (2 H, t, J = 5.1 Hz), 3.37 (4 H, td, J = 6.5, 5.1 Hz), 1.60-0.80 (48 H, m) | DMSO-$d_6$ |
| 14 | 8.20 (1 H, s, $J_{Sn-C-C-H}$ = 38.0 Hz), 8.02 (1 H, d, J = 7.8, Hz), 7.69 (1 H, d, J = 7.1 Hz, $J_{Sn-C-C-H}$ = 35.5 Hz), 7.41 (1 H, dd, J = 7.8, 7.1 Hz, $J_{Sn-C-C-C-H}$ = 8.0 Hz), 1.53 (6 H, m, $J_{Sn-C-C-C-H}$ = 50.2 Hz), 1.33 (6 H, m), 1.09 (6 H, m, $J_{Sn-C-C-H}$ = 51.4 Hz), 0.88 (9 H, t, J = 7.3 Hz). | CDCl$_3$ |
| 15 | 8.01 (1 H, s, $J_{Sn-C-C-H}$ = 38.7 Hz), 7.84 (1 H, d, J = 7.7 Hz), 7.62 (1 H, d, J = 7.1 Hz, $J_{Sn-C-C-H}$ = 35.9 Hz), 7.42 (1 H, dd, J = 7.7, 7.1 Hz), 6.44 (1 H, s, br), 6.35 (1 H, s, br), 4.29 (1 H, dd, J = 7.6, 5.1 Hz), 4.12 (1 H, ddd, J = 7.6, 4.4, 1.4 Hz), 4.00 (2 H, t, J = 6.0 Hz), 3.07 (1 H, ddd, J = 8.4, 6.1, 4.4 Hz), 2.81 (1 H, dd, J = 12.4, 5.1 Hz), 2.57 (1 H, d, J = 12.4 Hz), 2.24 (2 H, t, J = 7.5 Hz), 1.63-0.80 (30 H, m) | DMSO-$d_6$ |
| 16 | 8.18 (1 H, s, $J_{Sn-C-C-H}$ = 38.7 Hz), 8.00 (1 H, d, J = 7.8 Hz), 7.65 (1 H, d, J = 7.1 Hz, $J_{Sn-C-C-H}$ = 36.2 Hz), 7.46 (2 H, d, J = 7.5 Hz), 7.42-7.32 (4 H, m), 5.86 (1 H, ddt, J = 16.6, 10.1, 6.4 Hz), 5.38 (2 H, s), 4.99 (1 H, dd, J = 16.6, 1.8 Hz), 4.90 (1 H, dd, J = 10.1, 1.8 Hz), 2.30 (2 H, td, J = 8.0, 6.4 Hz, $J_{Sn-C-C-H}$ = 52.6 Hz), 1.68-0.84 (20 H, m) | CDCl$_3$ |
| 17 | 8.17 (1 H, s, $J_{Sn-C-C-H}$ = 38.7 Hz), 7.99 (1 H, d, J = 7.8 Hz), 7.64 (1 H, d, J = 7.1 Hz, $J_{Sn-C-C-H}$ = 36.2 Hz), 7.45 (2 H, dd, | CDCl$_3$ |

TABLE A-continued

¹H NMR data for compounds

| Compound | Chemical shifts | Solvent |
|---|---|---|
|  | J = 7.8, 7.1 Hz), 7.42-7.32 (4 H, m), 5.37 (2 H, s), 3.63 (2 H, m), 1.76-0.83 (24 H, m) |  |
| 18 | 8.07 (1 H, s, $J_{Sn-C-C-H}$ = 38.3 Hz), 7.92 (1 H, d, J = 7.8 Hz), 7.72 (1 H, d, J = 7.1 Hz, $J_{Sn-C-C-H}$ = 36.0 Hz), 7.49 (1 H, dd, J = 7.8, 7.1 Hz, $J_{Sn-C-C-C-H}$ = 8.6 Hz), 7.46 (2 H, d, J = 7.4 Hz), 7.40 (2 H, dd, J = 7.4, 7.3 Hz), 7.35 (1 H, t, J = 7.3 Hz), 6.69 (1 H, s), 6.60 (1 H, s), 5.35 (2 H, s), 4.41 (1 H, dd, J = 10.1, 7.1 Hz), 4.37 (1 H, ddd, J = 10.1, 6.1, 1.7 Hz), 3.99 (2 H, t, J = 5.9 Hz), 3.30 (1 H, dd, J = 14.1, 7.1 Hz), 3.15 (1 H, m), 3.02 (1 H, d, J = 14.1 Hz), 2.25 (2 H, t, J = 7.5 Hz), 1.71-0.79 (30H, m) | DMSO-$d_6$ |
| 19 | 8.07 (1 H, s, $J_{Sn-C-C-H}$ = 38.3 Hz), 7.92 (1 H, d, J = 7.9 Hz), 7.72 (1 H, d, J = 7.1 Hz, $J_{Sn-C-C-H}$ = 36.0 Hz), 7.48 (1 H, dd, J = 7.9, 7.1 Hz, $J_{Sn-C-C-C-H}$ = 8.6 Hz), 7.45 (2 H, d, J = 7.4 Hz), 7.39 (2 H, t, J = 7.4 Hz), 7.35 (1 H, t, J = 7.4 Hz), 6.42 (1 H, s), 6.36 (1 H, s), 5.35 (2 H, s), 4.28 (1 H, m), 4.11 (1 H, m), 3.98 (2 H, t, J = 5.8 Hz), 3.06 (1 H, ddd, J = 8.7, 6.1, 4.7 Hz), 2.80 (1 H, dd, J = 12.4, 5.1 Hz), 2.57 (1 H, d, J = 12.4 Hz), 2.22 (2 H, t, J = 7.5 Hz), 1.64-0.77 (30 H, m) | DMSO-$d_6$ |
| (t-Bu)-21 | 6.79 (1 H, s), 6.74 (1 H, s), 6.33 (1 H, s, br), 4.58 (1 H, dd, J = 7.8, 4.9 Hz), 4.39 (1 H, dd, J = 7.8, 4.6 Hz), 3.71 (2 H, t, J = 6.4 Hz), 3.66-3.53 (10 H, m), 3.44 (2 H, m), 3.19 (1 H, m), 2.94 (1 H, dd, J = 13.0, 4.9 Hz), 2.77 (1 H, d, J = 13.0 Hz), 2.50 (2 H, t, J = 6.4 Hz), 2.27 (2 H, m), 1.77-1.62 (4 H, m), 1.46 (2 H, m), 1.44 (9 H, s) | CDCl$_3$ |
| 22 | 8.07 (1 H, s, $J_{Sn-C-C-H}$ = 37.8 Hz), 7.92 (1 H, d, J = 7.9 Hz), 7.80 (1 H, t, J = 5.7 Hz), 7.72 (1 H, d, J = 7.2 Hz, $J_{Sn-C-C-H}$ = 36.3 Hz), 7.48 (1 H, dd, J = 7.9, 7.2 Hz, $J_{Sn-C-C-C-H}$ = 8.6 Hz), 7.45 (2 H, d, J = 7.6 Hz), 7.40 (2 H, t, J = 7.5 Hz), 7.35 (1 H, dd, J = 7.6, 7.5 Hz), 6.41 (1 H, s), 6.35 (1 H, s), 5.35 (2 H, s), 4.29 (1 H, dd, J = 7.6, 5.3 Hz), 4.11 (1 H, ddd, J = 7.6, 4.5, 1.9 Hz), 4.00 (2 H, t, J = 5.8 Hz), 3.58 (2 H, t, J = 6.2 Hz), 3.49-3.43 (8 H, m), 3.37 (2 H, t, J = 6.0 Hz), 3.17 (2 H, q, J = 5.9 Hz), 3.08 (1 H, ddd, J = 8.6, 6.2, 4.5 Hz), 2.81 (1 H, dd, J = 12.4, 5.1 Hz), 2.57 (1 H, d, J = 12.4 Hz), 2.47 (2 H, t, J = 6.2 Hz), 2.06 (2 H, t, J = 7.6 Hz), 1.64-0.80 (30 H, m) | DMSO-$d_6$ |

Note:
NMR spectra were recorded on Bruker AVIII 700 MHz NMR spectrometer and calibrated using residual undeuterated solvent as an internal reference. The following abbreviations were used to explain the multiplicities: s = singlet, d = doublet, t = triplet, q = quartet, br = broad. In ¹H NMR, averages of $J^{117}_{Sn-H}$ and $J^{119}_{Sn-H}$ were recorded due to severe overlapping of signals.

Example 2

Stability Studies

The stability of 18 and 19 with different oxidants used for radioiodination was explored without adding iodide to verify that biotin or biotin sulfone are compatible with oxidants used in radioiodination reactions.

Iodogen Test:

To an iodogen (20 μg) coated Eppendorf vial was added precursor (50 μg in 50 μL of MeOH containing 5% AcOH). The mixture was shaken gently at room temperature for 10-30 min then quenched with Na$_2$S$_2$O$_5$ (100 μL, 0.1 M, aq.). A small sample of the resulting clear solution was examined by LC-MS.

Iodination Bead or Peracetic Acid Test:

To an Eppendorf vial containing precursor (50 μg in 50 μL of MeOH containing 5% AcOH), was added the oxidant (one iodination bead or 5 μL of 30% peracetic acid). The mixture was shaken gently at room temperature for 10 min-120 min then quenched with Na$_2$S$_2$O$_5$ (100 μL, 0.1 M, aq.). A small sample of the resulting clear solution was examined by LC-MS.

It was observed that biotin 19 was stable in 5% AcOH/MeOH; acid catalyzed hydrodestannylation was not observed after 72 h (see FIG. 1A). Treating 19 in an iodogen-coated vial led to a complex product mixture; LC-MS showed that none of the new peaks are biotin sulfone or biotin sulfoxides (FIG. 1B). Iodobeads, a solid-supported chlorosulfonamide, reacted with 19 much more slowly (FIG. 1C). Peracetic acid on the other hand, oxidized 19 very cleanly to a mixture of biotin sulfone and biotin sulfoxides (FIGS. 1D and 1E).

Figure 2:
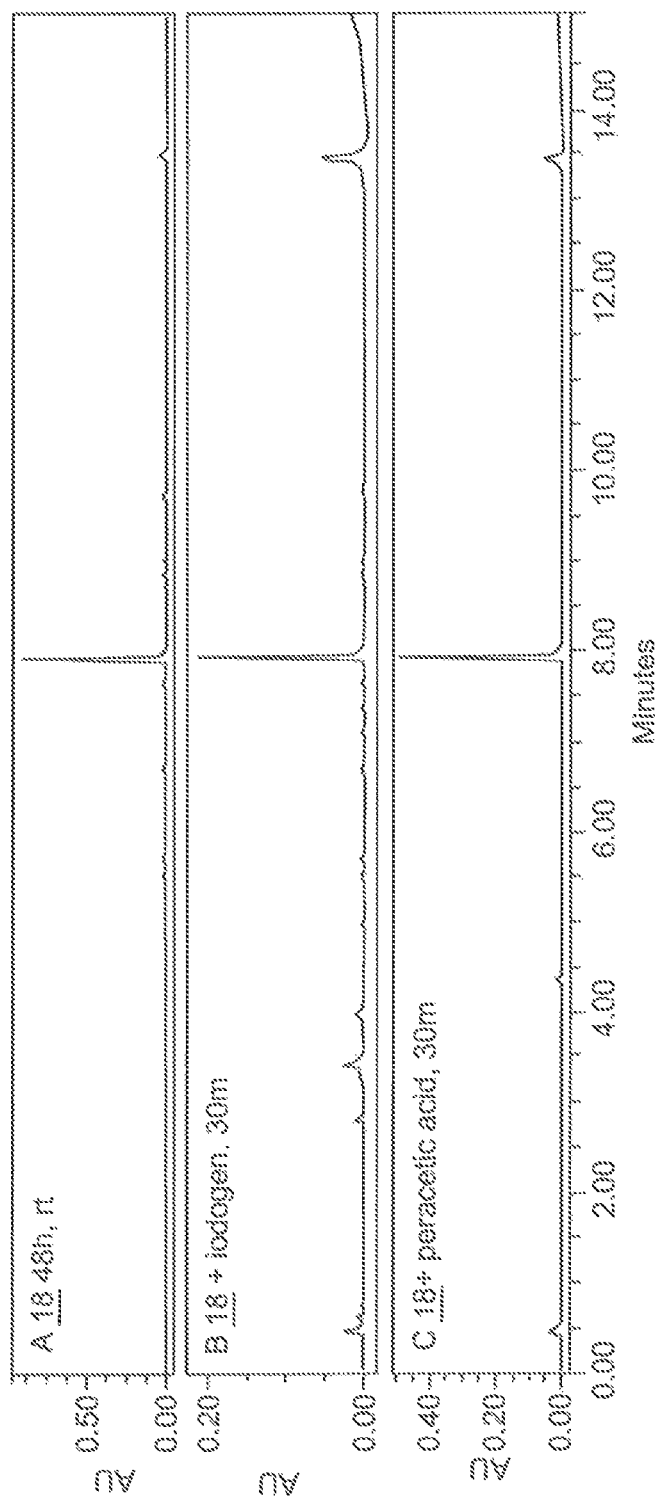
FIGS. 2A-2C are graphs demonstrating the stability of exemplary biotin sulfone precursors of the present teachings towards various oxidants used in radioiodination.

Biotin sulfone 18 is more stable towards oxidants; only minor oxidation products were observed (see FIG. 2).

Example 3

Iodination and Radioiodination Studies

Iodination and $^{125}$I radioiodination of precursors, such as biotin sulfone 2, were investigated with iodogen or peracetic acid as oxidant. Exemplary radioiodination is shown below in Scheme 9.

Scheme 9

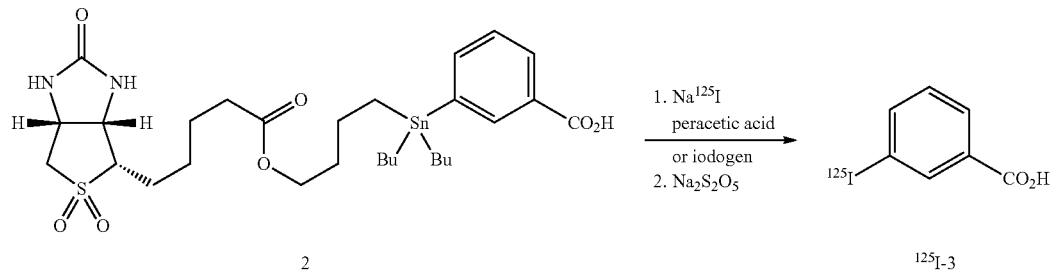

Iodination (Cold/Non-Radioactive) Procedure:

To an iodogen (20 µg) coated Eppendorf vial was added precursor (50 µg in 50 µL of EtOH or MeOH containing 5% AcOH) followed by NaI (5 µg in 10 µL $H_2O$). The mixture was shaken gently at room temperature for 5 min then quenched with $Na_2S_2O_5$ (100 µL, 0.1 M, aq.). A small sample of the resulting clear solution was examined by LC-MS to determine extent of reaction.

Cold studies were performed on Waters Acquity UPLC system using a Waters Acquity Analytical UPLC column (100×2.1 mm, C18, 1.7 µm BEH). The Mobile Phase consisted of Solvent A ($H_2O$, 0.1% TFA) and Solvent B (Acetonitrile, 0.1% TFA) at a flow rate of 0.30 ml/min. The amount of Solvent B varied over time as given below in Table 1.

TABLE 1

| Time (mins) | 0 | 8 | 12.5 | 13 | 15 |
|---|---|---|---|---|---|
| % B | 10 | 100 | 100 | 10 | 10 |

$^{25}$I Radioiodination (hot) Procedure with Iodogen:

To an iodogen (20 µg) coated Eppendorf vial was added precursor (50 µg in 50 µL of EtOH or MeOH with 5% AcOH) followed by $Na^{125}I$ (7.4 MBq [200 µCi], in 10 µL 0.1 N NaOH). The mixture was shaken gently at room temperature for 10 min then quenched with $Na_2S_2O_5$ (100 µL, 0.1 M, aq.). A small sample of the resulting clear solution was examined by HPLC.

$^{125}$I Radioiodination (Hot) Procedure with Peracetic Acid:

To an Eppendorf vial was added precursor (50 µg in 50 µL of EtOH or MeOH containing 5% AcOH) followed by $Na^{125}I$ (7.4 MBq [200 µCi], in 10 µL 1 N NaOH) and peracetic acid (5 µL, 30% aq.). The mixture was shaken gently at room temperature for 10 min then quenched with $Na_2S_2O_5$ (100 µL, 0.1 M, aq.). A small sample of the resulting clear solution was examined by HPLC.

HPLC studies were performed on Waters HPLC system using an X-Bridge Analytical HPLC column (100×4.6 mm, C18, 2.3 micron). The Mobile Phase consisted of Solvent A ($H_2O$, 0.4% ammonium formate) and Solvent B (MeOH) at a flow rate of 0.8 ml/min. The amount of Solvent B varied over time as given below in Table 2.

TABLE 2

| Time (mins) | 0 | 6 | 15 | 16 | 20 |
|---|---|---|---|---|---|
| % B | 60 | 100 | 100 | 60 | 60 |

Figure 4:
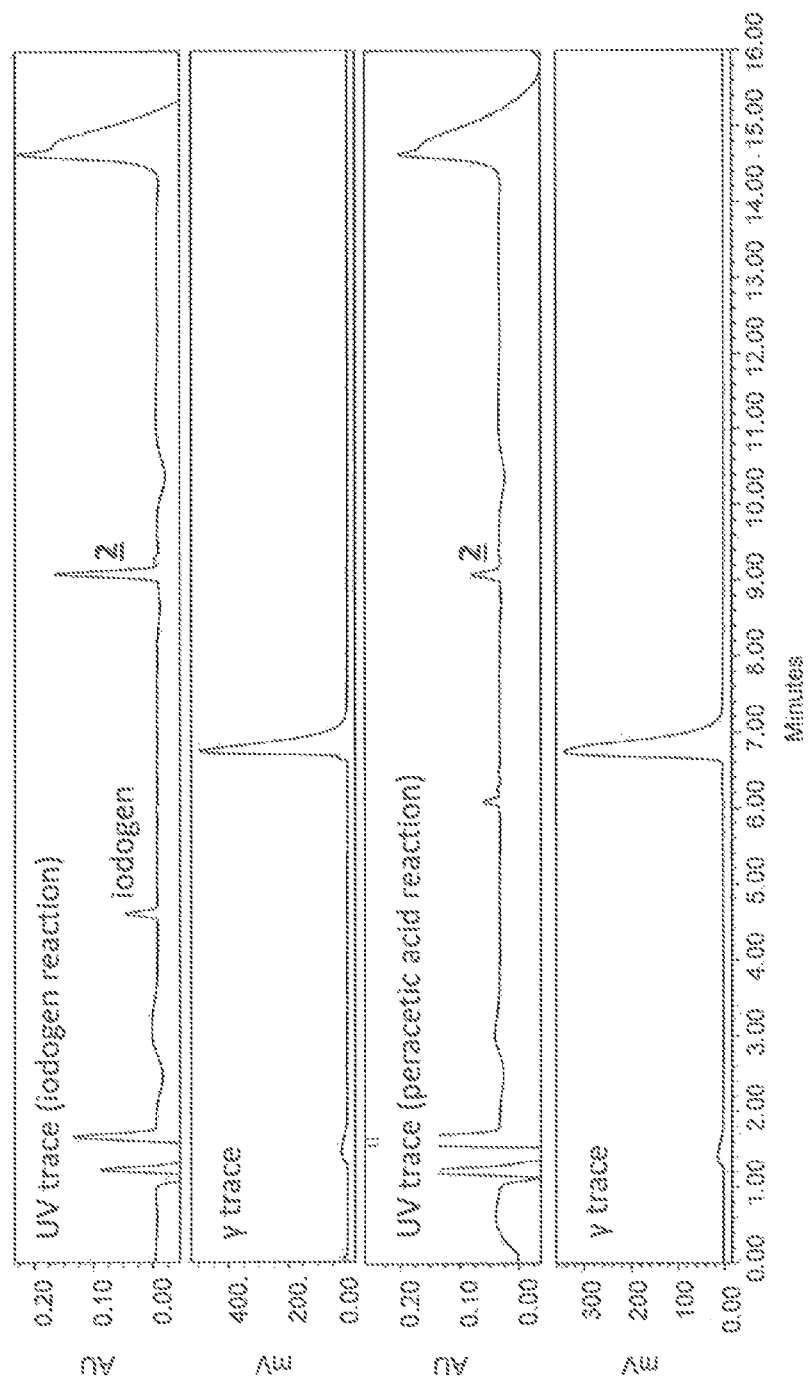
FIGS. 4 and 5 depict UV and γ traces of an exemplary radioiodinated product of the present teachings, before and after purification.

FIG. 4 shows the results of $^{125}$I radioiodination of biotin sulfone 2. Peracetic acid generated a small additional product (shown at 6 min on the UV spectrum) whereas iodogen generated no additional products on the UV chromatogram, though the reduced iodogen is evident. Both labeling reactions produced desired product $^{125}$I-3 with excellent radiochemical purity (>95%).

Example 4

Streptavidin Binding Studies

Figure 3:
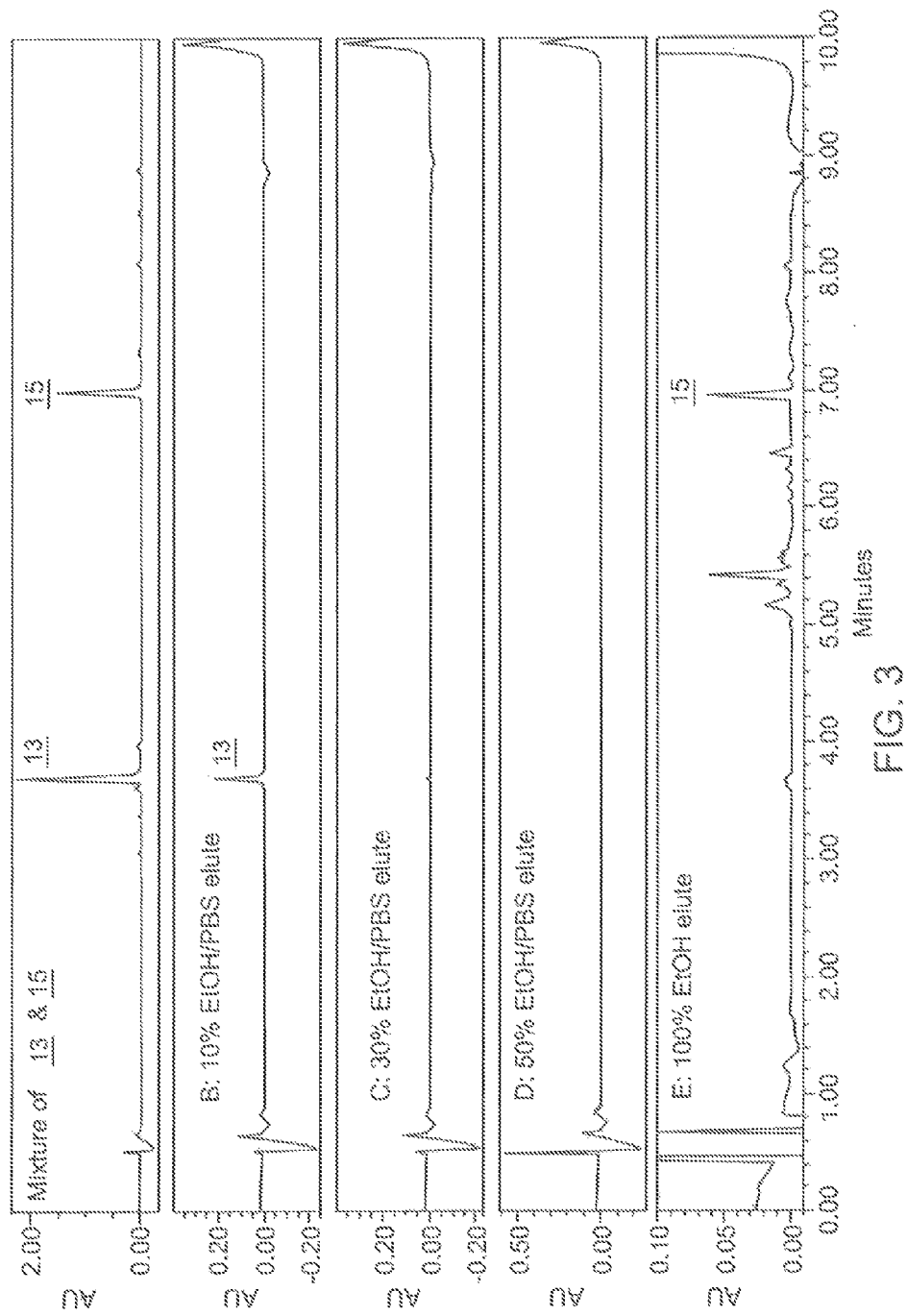
FIGS. 3A-3E are graphs demonstrating the ability of streptavidin resin to retain exemplary precursors of the present teachings at various solvent ratios.

Before attempting labeling studies, the ability of streptavidin resin to retain precursors, e.g., compound 15, was evaluated. 1.0 mL of high-capacity streptavidin resin (dispensed as 2.0 mL of 50% slurry in water) was loaded onto a 1.5-mL empty cartridge and was washed with 10% EtOH in PBS (5 mL). A mixture of 3 and 15 was prepared in 10% EtOH/PBS (250 µL) and loaded (400 µL total volume) onto the prepacked high-capacity streptavidin agarose resin column. After 20 min incubation, the column was flushed with a mixture of EtOH/PBS (from 10% EtOH/PBS to 100% EtOH) and 1 mL fractions were collected. HPLC traces of the eluent are shown in FIG. 3. As expected, 3 eluted with 10% EtOH/PBS, while 15 was retained on the column. Elution of biotin-tin acid 15 was only observed when in the 100% EtOH wash. Similar behavior was observed for biotin sulfone precursor 2.

These results suggest that the biotin sulfone-streptavidin or biotin-streptavidin interaction is can be used in separating non-biotin containing molecules from biotin modified stannanes. Therefore, either biotin sulfone precursors, such as 2 and 18, or biotin containing precursors, such as 15, 19 and 22, may be used in the methods described herein.

Example 5

Purification Study

Figure 5:
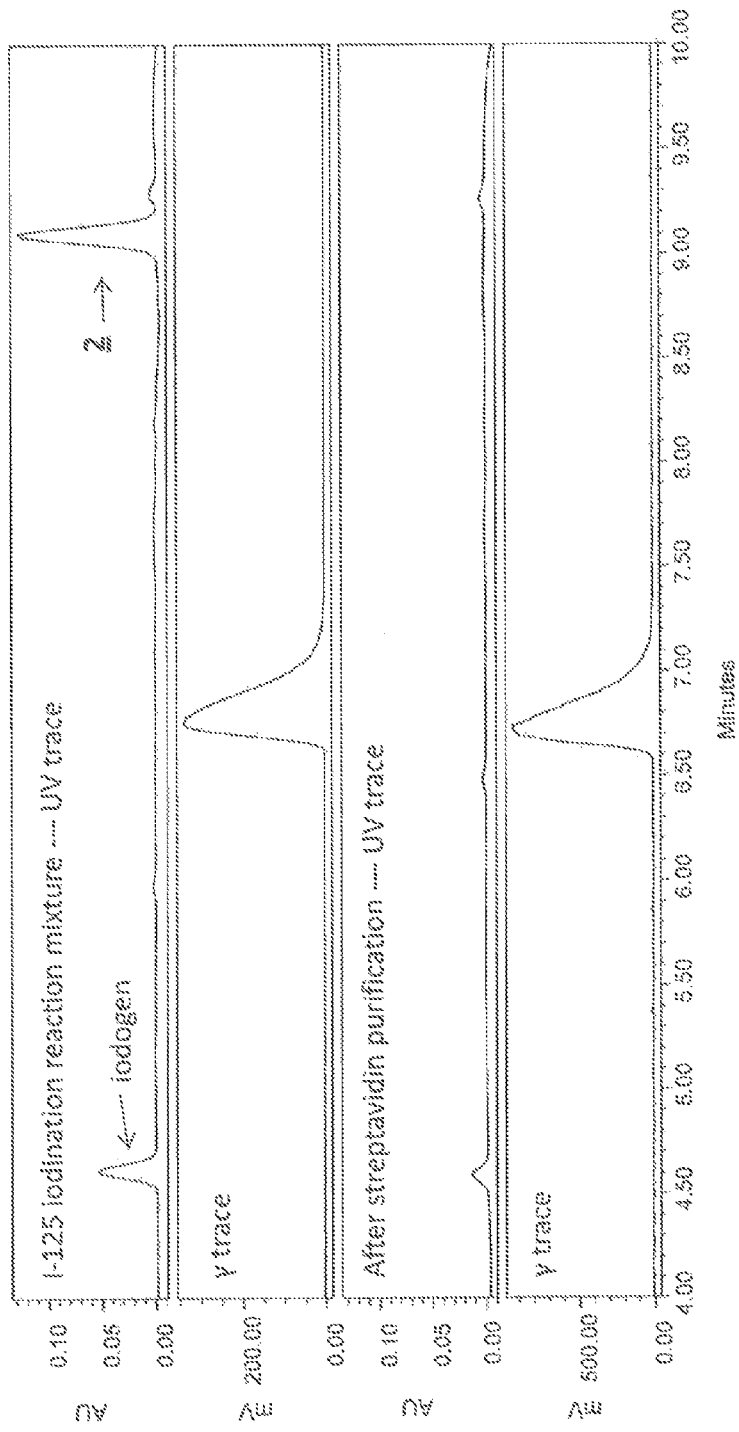

The $^{125}$I radiolabeling reaction mixture of 2 and iodogen was purified using a streptavidin resin column. Using previously developed conditions, such as those described above in Example 4, the labeling mixture was diluted with 10% EtOH/PBS and loaded onto a prepacked streptavidin resin column. After 20 minutes of incubation, the column was flushed with 10% EtOH/PBS (1 cv). As shown in FIG. 5, 99% activity was recovered and no residual 2 was detected by HPLC. Thus biotin sulfone-straptavidin technology may be readily used for HPLC-free radioiodination Example 6

Solubility Enhancing Agent Study

Radioiodination of hydrophobic benzyl ester precursor 4 to yield desired radioiodinated product $^{125}$I-3IBABn did not yield significant product after passage through a streptavidin functionalized resin; nearly all the radioactivity was retained on the resin under previously described conditions. However, the addition 10%, 20% and 40% Hydroxypropyl-β-cyclodextrin (HP-β-CD) w/v after reaction improved the yield of purified $^{125}$I-3IBABn to 93%.

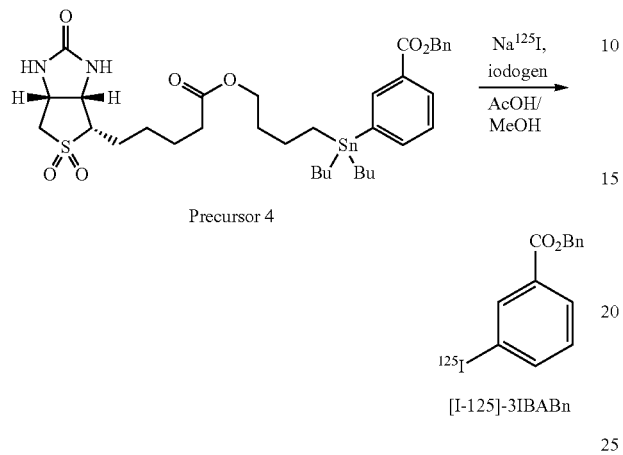

Precursor 4

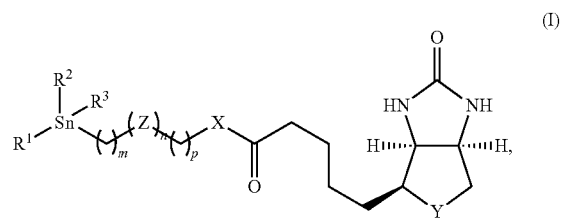

[I-125]-3IBABn

Radiolabeling Procedure:

To an Eppendorf vial were added 56.6 µg precursor 4 (56.6 µL, 1.0 mg/mL, EtOH), 5 µL AcOH, Na$^{125}$I (18.5 MBq or 500 µCi, pH 8~11 in aqueous NaOH) and iodogen (50 µL, 0.2 mg/mL in EtOH), subsequently. The reaction mixture was allowed to sit at room temperature for 20 minutes, with occasional swirling. After quenching with 100 µL of Na$_2$S$_2$O$_3$ (0.1 M aq.), the mixture was diluted with 100 µL of EtOH then added to the binding buffer tested as described below.

General Procedure for the Purification with Streptavidin Resin Column in the Presence of Additives:

A streptavidin resin column was packed using 1.6 mL of resin slurry (0.8 mL of actual resin) as described previously and washed with the appropriate binding buffer (4.0 mL, 5 cv). An 80 µL aliquot of the above radiolabeling mixture was diluted with the appropriate binding buffer (920 µL) and mixed for 10 minutes before loading onto streptavidin column. After incubation for 20 minutes, radiolabeled product was eluted off the column with binding buffer (three 0.5 mL fractions collected). All fractions (including a forerun fraction collected while loading the reaction mixture onto column) were subjected to HPLC analysis before being combined.

Binding Buffer Tested:
10% EtOH in PBS (control experiment)
10% (wt/v) HP-β-CD in PBS
20% (wt/v) HP-β-CD in PBS
40% (wt/v) HP-β-CD in PBS

| Eluent | % HP-CD in eluent | Activity left on column |
|---|---|---|
| 10% EtOH in PBS (control experiment) | 0% | 91% |
| PBS (HP-β-CD, w/v) | 10% | 16% |
| | 20% | 13% |
| | 40% | 7% |

EQUIVALENTS

Those skilled in the art will recognize, or be able to ascertain using no more than routine experimentation, numerous equivalents to the specific procedures described herein. Such equivalents are considered to be within the scope of the present invention and are covered by the following claims.

We claim:

1. A method of preparing a radioiodinated compound, the method comprising:
   contacting a precursor with a radioactive iodide and an oxidant to form a reaction mixture comprising a radioiodinated compound, unreacted precursor, and reaction byproducts; and
   contacting the reaction mixture with avidin or streptavidin; thereby separating the radioiodinated compound from the precursor and the reaction byproducts; wherein the precursor is a compound of formula (I):

(I)

or a pharmaceutically acceptable salt thereof; wherein:
$R^1$ is an aromatic or vinyl group capable of being substituted at an aromatic or vinylic carbon with iodide;
$R^2$ and $R^3$ are each independently selected from $R^1$; alkyl or alkoxyalkyl, each substituted with 0-4 $R^5$ groups; or $R^2$ and $R^3$, along with the Sn atom to which they are attached, form a 3 to 8-membered ring that optionally includes one or more heteroatom selected from N, O, or S;
Z is selected from —(C$_1$-C$_4$)alkylene-, —(C$_1$-C$_4$)alkylene-O—, arylene, heteroarylene, cycloalkylene or heterocycloalkylene, provided that m is at least 1 when Z is arylene or heteroarylene, and n=1 to 9, and provided that p=2-10 when Z is —(C$_1$-C$_4$)alkylene-O—;
X is selected from —O— or —NR$^4$—;
$R^4$ is selected from H or alkyl, wherein the alkyl is substituted with 0-4 $R^6$ groups;
each $R^5$ is independently selected from —H, -halogen, —CN, —NO$_2$, —NR$^a$R$^b$, —S(O)$_i$R$^c$, —C(=O)R$^c$, —C(=O)OR$^c$, or —OC(=O)R$^c$;
$R^6$ is selected from —H, -halogen, —CN, —NO$_2$, —NR$^a$R$^b$, —OR$^c$, —S(O)$_i$R$^c$, —C(=O)R$^c$, —C(=O)OR$^c$, or —OC(=O)R$^c$;
$R^a$, $R^b$ and $R^c$ are each independently selected from —H or (C$_1$-C$_6$)alkyl;
Y is selected from S, SO, SO$_2$ or O;
i is 0, 1, or 2; and
m, n and p are each independently an integer from 0 to 10, wherein m+n+p≥1.

2. The method of claim 1, further comprising contacting the reaction mixture with a solubility enhancing agent.

3. The method of claim 2, the method comprising:
   contacting the precursor with the radioactive iodide, the oxidant, and the solubility enhancing agent to form the reaction mixture comprising the radioiodinated compound, the solubility enhancing agent, unreacted precursor, and reaction byproducts; and
   contacting the reaction mixture with avidin or streptavidin; thereby separating the radioiodinated compound from the precursor and the reaction byproducts.

4. The method of claim 2, the method comprising:
contacting the precursor with the radioactive iodide, and the oxidant to form the reaction mixture comprising the radioiodinated compound, unreacted precursor, and reaction byproducts; and
contacting the reaction mixture with the solubility enhancing agent and avidin or streptavidin; thereby separating the radioiodinated compound from the precursor and the reaction byproducts.

5. The method of claim 1, the method comprising:
contacting the precursor with the radioactive iodide and the oxidant to form the reaction mixture comprising the radioiodinated compound, unreacted precursor, and reaction byproducts;
contacting the reaction mixture with a reductant to form a reduced reaction mixture; and
contacting the reduced reaction mixture with avidin or streptavidin; thereby separating the radioiodinated compound from the precursor and the reaction byproducts.

6. The method of claim 5, further comprising the step of contacting the reaction mixture or the reduced reaction mixture with a solubility enhancing agent.

7. The method of claim 6, the method comprising:
contacting the precursor with the radioactive iodide, the oxidant and the solubility enhancing agent to form the reaction mixture comprising the radioiodinated compound, the solubility enhancing agent, unreacted precursor, and reaction byproducts;
contacting the reaction mixture with the reductant to form the reduced reaction mixture; and
contacting the reduced reaction mixture with avidin or streptavidin; thereby separating the radioiodinated compound from the precursor and the reaction byproducts.

8. The method of claim 6, the method comprising:
contacting the precursor with the radioactive iodide and the oxidant to form the reaction mixture comprising the radioiodinated compound, unreacted precursor, and reaction byproducts;
contacting the reaction mixture with the reductant to form the reduced reaction mixture; and
contacting the reduced reaction mixture with the solubility enhancing agent and avidin or streptavidin; thereby separating the radioiodinated compound from the precursor and the reaction byproducts.

9. The method of claim 1, wherein the radioiodinated compound comprises an aryl moiety.

10. The method of claim 1, wherein the radioiodinated compound comprises a vinyl moiety.

11. The method of claim 1, wherein the radioiodinated compound is selected from a radioiodinated benzoic acid, a radioiodinated benzamide, a radioiodinated benzylamine, or a radioiodinated benzylguanidine.

12. The method of claim 1, wherein $R^2$ and $R^3$ are each independently selected from ($C_1$-$C_6$)alkyl or alkoxyalkyl.

13. The method of claim 1, wherein $R^2$ and $R^3$ are each independently selected from methyl, ethyl, n-propyl, or n-butyl.

14. The method of claim 1, wherein X is selected from O or $NR^4$; and $R^4$ is selected from H or ($C_1$-$C_6$)alkyl.

15. The method of claim 1, wherein X is selected from O or NH.

16. The method of claim 1, wherein Y is selected from O, S, SO, or $SO_2$.

17. The method of claim 1, wherein Y is $SO_2$.

18. The method of claim 1, wherein Z is —($C_1$-$C_4$)alkylene-O—.

19. The method of claim 1, wherein m, n and p are each independently an integer from 0 to 5.

20. The method of claim 1, wherein m and n are both 0 and p is an integer from 2 to 4.

21. The method of claim 1, wherein the radioactive iodide is selected from $^{123}I$, $^{124}I$, $^{125}I$, or $^{131}I$.

22. The method of claim 1, wherein the oxidant is selected from iodogen or peracetic acid.

23. The method of claim 22, wherein the oxidant is pre-coated onto a tube or bead.

24. The method of claim 1, wherein contacting the reaction mixture with avidin or streptavidin further comprises:
passing the reaction mixture down a column of avidin or streptavidin solid support; or
mixing an avidin or streptavidin solid support with the reaction mixture followed by filtering; or
depositing the precursor on an avidin or streptavidin solid support, followed by contacting the precursor with the radioactive iodide and the oxidant, followed by eluting the radioiodinated compound; or
treating the reaction mixture with soluble avidin or streptavidin followed by size separation of avidin- or streptavidin-bound complexes from the radioiodinated compound; or
passing the reaction mixture over a streptavidin or avidin-coated surface.

25. A compound of formula (I):

or a pharmaceutically acceptable salt thereof; wherein:
$R^1$ is an aromatic or vinyl group capable of being substituted at an aromatic or vinylic carbon with iodide;
$R^2$ and $R^3$ are each independently selected from $R^1$; alkyl or alkoxyalkyl, each substituted with 0-4 $R^5$ groups; or $R^2$ and $R^3$, along with the Sn atom to which they are attached, form a 3 to 8-membered ring that optionally includes one or more heteroatom selected from N, O, or S;
Z is selected from —($C_1$-$C_4$)alkylene-, —($C_1$-$C_4$)alkylene-O—, arylene, heteroarylene, cycloalkylene or heterocycloalkylene, provided that m is at least 1 when Z is arylene or heteroarylene;
X is selected from —O—, and —$NR^4$—;
$R^4$ is selected from H and alkyl, wherein the alkyl is substituted with 0-4 $R^6$ groups;
each $R^5$ is independently selected from —H, -halogen, —CN, —$NO_2$, —$NR^aR^b$, —$OR^c$, —$S(O)_tR^c$, —C(=O)$R^c$, —C(=O)O$R^c$ and —OC(=O)$R^c$;
$R^6$ is selected from —H, -halogen, —CN, —$NO_2$, —$NR^aR^b$, —$OR^c$, —$S(O)_tR^c$, —C(=O)$R^c$, —C(=O)O$R^c$ and —OC(=O)$R^c$;
$R^a$, $R^b$ and $R^c$ are each independently selected from —H and ($C_1$-$C_6$)alkyl;
Y is selected from S, SO, $SO_2$ and O; and
m, n and p are each independently an integer from 0 to 10, wherein m+n+p≥1.

26. A compound of formula (I):

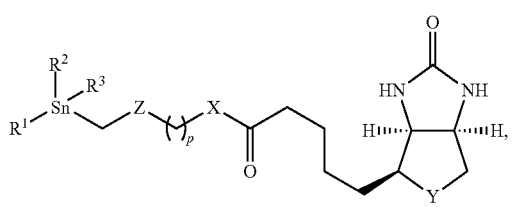

or a pharmaceutically acceptable salt thereof; wherein:
- $R^1$ is an aromatic or vinyl group capable of being substituted at an aromatic or vinylic carbon with iodide;
- $R^2$ and $R^3$ are each independently selected from ($C_1$-$C_6$) alkyl or alkoxyalkyl; or $R^2$ and $R^3$, along with the Sn atom to which they attach, form a 4, 5 or 6-membered ring that optionally includes one or more heteroatom selected from N, O, or S;
- Z is —($C_1$-$C_4$)alkylene-O—;
- X is selected from 0 and NH;
- Y is selected from S or $SO_2$; and
- p is an integer from 2 to 4.

27. The method of claim 5, wherein contacting the reduced reaction mixture with avidin or streptavidin further comprises:
- passing the reduced reaction mixture down a column of avidin or streptavidin solid support; or
- mixing an avidin or streptavidin solid support with the reduced reaction mixture followed by filtering; or
- depositing the precursor on an avidin or streptavidin solid support, followed by contacting the precursor with the radioactive iodide and the oxidant, followed by eluting the radioiodinated compound; or
- treating the reduced reaction mixture with soluble avidin or streptavidin followed by size separation of avidin- or streptavidin-bound complexes from the radioiodinated compound; or
- passing the reduced reaction mixture over a streptavidin or avidin-coated surface.

* * * * *